US011259712B2

United States Patent
Lee et al.

(10) Patent No.: US 11,259,712 B2
(45) Date of Patent: Mar. 1, 2022

(54) WEARABLE REFLECTANCE-MODE PPG SENSOR NETWORK HAVING IMPROVED DETECTED SIGNAL STRENGTH

(71) Applicant: International Business Machines Corporation, Armonk, NY (US)

(72) Inventors: Kang-Wook Lee, Yorktown Heights, NY (US); Rajeev Narayanan, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 545 days.

(21) Appl. No.: 16/189,294

(22) Filed: Nov. 13, 2018

(65) Prior Publication Data

US 2020/0146569 A1    May 14, 2020

(51) Int. Cl.
*A61B 5/024*    (2006.01)
*A61B 5/00*    (2006.01)
*A61B 5/1455*    (2006.01)

(52) U.S. Cl.
CPC ...... *A61B 5/02433* (2013.01); *A61B 5/02438* (2013.01); *A61B 5/1455* (2013.01); *A61B 5/681* (2013.01); *A61B 5/7221* (2013.01); *A61B 2562/0238* (2013.01)

(58) Field of Classification Search
CPC ............ A61B 5/02433; A61B 5/02438; A61B 5/14552; A61B 5/681; A61B 5/6824; A61B 5/7221; A61B 2562/0238
See application file for complete search history.

(56) References Cited

U.S. PATENT DOCUMENTS

| 6,432,060 | B1 | 8/2002 | Amano |
| 6,602,198 | B2 | 8/2003 | Yokozeki |
| 9,775,548 | B2* | 10/2017 | Sarantos ............ A61B 5/14552 |
| 10,098,611 | B2 | 10/2018 | Lee et al. |
| 10,271,745 | B2* | 4/2019 | Gu ........................ A61B 5/6828 |
| 10,568,525 | B1* | 2/2020 | Wu .................... A61B 5/14552 |
| 10,776,455 | B2 | 9/2020 | Reddy et al. |

(Continued)

FOREIGN PATENT DOCUMENTS

| GB | 2517179 A | 2/2015 |
| WO | 2016017930 A1 | 2/2016 |

OTHER PUBLICATIONS

Ding et al., "Continuous Cuffless Blood Pressure Estimation Using Pulse Transit Time and Photoplethysmogram Intensity Ratio," IEEE Transactions on Biomedical Engineering 63.5, 2016, pp. 964-972.

(Continued)

*Primary Examiner* — Eric F Winakur
(74) *Attorney, Agent, or Firm* — Cantor Colburn LLP; Kristofer Haggerty

(57) ABSTRACT

Embodiments of the invention are directed to a photoplethysmogram (PPG) structure that includes a wearable component and a network of PPG sensors physically coupled to the wearable component. Each PPG sensor of the network includes a housing, a first light source and a light detector. The first light source is positioned in or on the housing such that, when the housing is positioned on a surface, the housing positions an illuminating surface of the first light source at a predetermined first-light-source angle with respect to the surface.

20 Claims, 11 Drawing Sheets

(56) References Cited

U.S. PATENT DOCUMENTS

| | | | |
|---|---|---|---|
| 2009/0054751 A1* | 2/2009 | Babashan | A61B 5/14552 600/324 |
| 2014/0012146 A1 | 1/2014 | Fukuda | |
| 2014/0288390 A1* | 9/2014 | Hong | A61B 5/02416 600/301 |
| 2015/0157220 A1* | 6/2015 | Fish | A61B 5/14552 600/301 |
| 2017/0172476 A1 | 6/2017 | Schilthuizen | |
| 2017/0209055 A1 | 7/2017 | Pantelopoulos et al. | |
| 2017/0245767 A1 | 8/2017 | Ferber et al. | |
| 2017/0340209 A1 | 11/2017 | Klaassen et al. | |
| 2018/0000363 A1 | 1/2018 | Pekonen et al. | |
| 2018/0078153 A1 | 3/2018 | Knickerbocker et al. | |
| 2018/0078154 A1 | 3/2018 | Knickerbocker et al. | |
| 2018/0116534 A1 | 5/2018 | Tal et al. | |
| 2019/0133533 A1* | 5/2019 | Alam | A61B 5/7221 |

OTHER PUBLICATIONS

Fuke et al., "Blood pressure estimation from pulse wave velocity measured on the chest," 35th Annual International Conference of the IEEE Engineering in Medicine and Biology Society, 2013, pp. 6107-6110.

Fung et al., "Continuous Noninvasive Blood Pressure Measurement by Pulse Transit Time," Proceedings of the 26th Annual International Conference of the IEEE Engineering in Medicine and Biology Society, Sep. 2004, pp. 738-741.

Garbarino et al., "Empatica E3—A wearable wireless multi-sensor device for real-time computerized biofeedback and data acquisition," 2014 EAI 4th International Conference on Wireless Mobile Communication and Healthcare (Mobihealth), IEEE, 2014, 4 pages.

Gesche et al., "Continuous blood pressure measurement by using the pulse transit time: comparison to a cuff-based method," European Journal of Applied Physiology, vol. 112, No. 1, 2012, pp. 309-315.

Haahr et al., "A Novel Photodiode for Reflectance Pulse Oximetry in low-power applications," 2007 29th Annual International Conference of the IEEE Engineering in Medicine and Biology Society, IEEE, 2007, 5 pages.

Kao et al., "A New Cuffless Optical Sensor for Blood Pressure Measuring with Self-Adaptive Signal Processing," Proceedings of the 2016 IEEE Sensors, 2016, pp. 1108-1110.

List of IBM Patents or Patent Applications Treated as Related; Date Filed: Nov. 13, 2018, 2 pages.

Koon et al., "Non-constrained Blood Pressure Monitoring Using ECG and PPG for Personal Healthcare," Journal of Medical Systems 33.4, 2009, pp. 261-266.

A. Patzak et al., "Continuous blood pressure measurement using the pulse transit time: comparison to intra-arterial measurement," Blood Pressure, vol. 24, No. 4, 2015, pp. 217-221.

Goli et al., "Cuff less continuous non-invasive blood pressure measurement using pulse transit time measurement", International Journal of Recent Development in Engineering and Technology, vol. 2, No. 1, pp. 86-91, Jan. 2014.

Heravi et al., "A New Approach for Blood Pressure Monitoring based on ECG and PPG Signals by using Artificial Neural Networks." International Journal of Computer Applications (0975: 8887), vol. 103, No. 12, Oct. 2014, pp. 36-40.

Ilango et al., "A non-invasive blood pressure measurement using android smart phones." IOSR J Dent Med Sci 13.1 (2014): 28-31.

Kim et al., "A new approach on digital blood pressure measurement method for u-healthcare systems" International Journal of Bio-Science and Bio-Technology 7.1 (2015): 169-178.

Li et al., "Mechanism of cuff-less blood pressure measurement using MMSB." Engineering 5.10 (2013): 123-125.

McCarthy et al., "An investigation of pulse transit time as a non-invasive blood pressure measurement method." Journal of Physics: Conference Series. vol. 307. No. 1. IOP Publishing, 2011, 6 pages.

Nam et al., "Measurement of spatial pulse wave velocity by using a clip-type pulsimeter equipped with a Hall sensor and photoplethysmography." Sensors 13.4 (2013): 4714-4723.

Poon et al., "Cuff-less and noninvasive measurements of arterial blood pressure by pulse transit time." 2005 IEEE Engineering in Medicine and Biology 27th Annual Conference, 2006, pp. 5877-5880.

Thomas et al., "BioWatch: A noninvasive wrist-based blood pressure monitor that incorporates training techniques for posture and subject variability." IEEE journal of biomedical and health informatics 20.5 (2015): 1291-1300.

Zhang et al., "A LabVIEW based measure system for pulse wave transit time." 2008 Proceedings of the 5th International Conference on Information Technology and Application in Biomedicine, IEEE, 2008, pp. 477-480.

* cited by examiner

WEARABLE REFLECTANCE-MODE PPG SENSOR NETWORK HAVING IMPROVED DETECTED SIGNAL STRENGTH

BACKGROUND

The present invention relates generally to medical monitoring devices/sensors, and more specifically to providing wearable reflectance-mode photoplethysmogram (PPG) devices/sensors configured as a network and having improved detected signal strength.

The terms "PPG monitor" are used to refer, collectively, to any medical device or sensor that relies on some form of PPG technology to generate signals that measure a detected physical characteristic. PPG technology is the non-invasive optical measurement of oxygen saturation ($SpO_2$), which is defined as a measurement of the amount of oxygen dissolved in blood based on the detection of hemoglobin and deoxygenated hemoglobin. A light source (e.g., a light emitting diode (LED)) transmits two different light wavelengths through the skin, and a detector (e.g., a photodiode (PD)) measures the non-absorbed light that is either transmitted through (transmission mode) or reflected by (reflectance/reflective mode) the bone, veins, and other tissues below the skin. The non-absorbed light received at the detector is used to measure the actual difference in the absorption spectra of oxygenated hemoglobin ($HbO_2$) and deoxygenated hemoglobin (Hb). The bloodstream is affected by the concentration of $HbO_2$ and Hb, and their absorption coefficients can be measured using two wavelengths, namely 660 nm (red light spectra) and 940 nm (infrared light spectra). $HbO_2$ and Hb absorb different wavelengths. Hb has a higher absorption at 660 nm, and $HbO_2$ has a higher absorption at 940 nm. The non-absorbed light received at the detector is inverted using an inverting operational amplifier. The result is a signal that represents the light that has been absorbed by the body and is divided into a so-called "DC" component and an "AC" component. The DC component represents the light absorption of the tissue, venous blood, and non-pulsatile arterial blood. The AC component represents the pulsatile arterial blood. PPG technology has application in a variety of medical monitoring scenarios, including but not limited to, measuring oxygen saturation, measuring blood pressure, measuring cardiac output, assessing autonomic function, and detecting peripheral vascular disease.

SUMMARY

Embodiments of the invention are directed to a PPG structure that includes a wearable component and a network of PPG sensors physically coupled to the wearable component. Each PPG sensor of the network includes a housing, a first light source and a light detector. The first light source is positioned in or on the housing such that, when the housing is positioned on a surface, the housing positions an illuminating surface of the first light source at a predetermined first-light-source angle with respect to the surface.

Embodiments of the invention are further directed to a method of forming a PPG structure. The method includes providing a wearable component and a network of PPG sensors physically coupled to the wearable component. Each PPG sensor of the network includes a housing, a first light source and a light detector. The first light source is positioned in or on the housing such that, when the housing is positioned on a surface, the housing positions an illuminating surface of the first light source at a predetermined first-light-source angle with respect to the surface.

Additional features and advantages are realized through the techniques described herein. Other embodiments and aspects are described in detail herein. For a better understanding, refer to the description and to the drawings.

BRIEF DESCRIPTION OF THE DRAWINGS

The subject matter which is regarded as the present invention is particularly pointed out and distinctly claimed in the claims at the conclusion of the specification. The foregoing and other features and advantages are apparent from the following detailed description taken in conjunction with the accompanying drawings in which:

Figure 1:
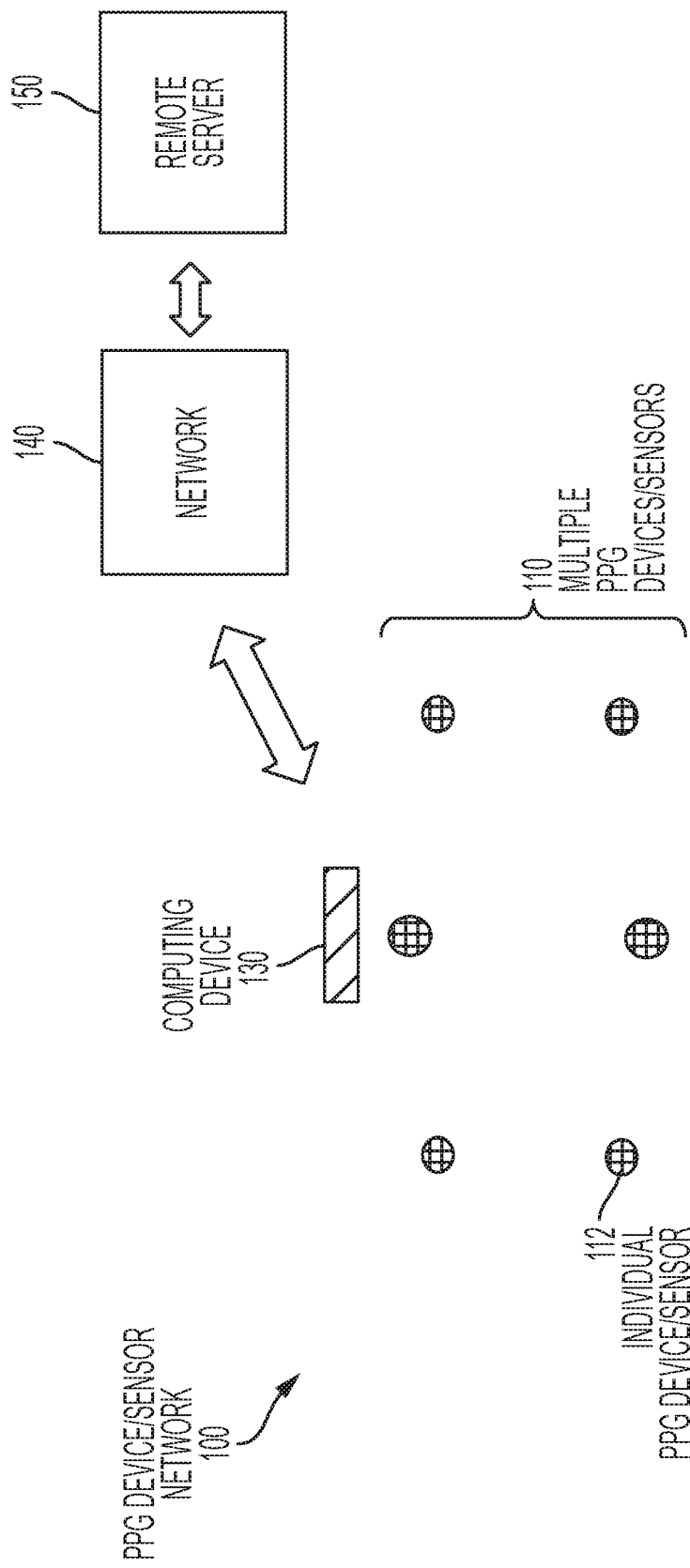
FIG. 1 is a block diagram of a PPG device network in accordance with embodiments of the invention.

In the accompanying figures and following detailed description of the disclosed embodiments, the various elements illustrated in the figures are provided with three digit reference numbers. The leftmost digit of each reference number corresponds to the figure in which its element is first illustrated.

DETAILED DESCRIPTION

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to a more detailed description of technologies that are more specifically related to aspects of the invention, the use of PPG technology in medical monitoring devices has increased with the increased demand for low cost, simple and portable technology for clinical settings; the wide availability of low cost and small semiconductor components; the wide availability of low cost portable computing devices and systems; and the advancement of computer-based pulse wave analysis techniques. With respect to low cost, portable computing devices/systems, improvements in the computational speed, size, and portability of computing devices/systems have enabled the continued integration of computer functionality into everyday life. For example, small mobile computing systems, such as miniaturized computers, input devices, sensors, detectors, image displays, wireless communication devices as well as image and audio processors, can be integrated into computing devices that fit easily in a user's pocket or travel bag. Hence, computing devices are now present in any environment where users are present. Miniaturized computers provide portable hand-held devices with enough hardware, software, and batter power to execute typical desktop and web-based applications. Miniaturized computers have similar hardware and software components as those used in personal computers (PCs), such as processors, random memory and storage, Wi-Fi, and a base operating system (OS). For example, a smart watch includes a built-in processor, memory and OS that are capable of executing a wide variety of computer software application programs. However, they differ from PCs in that they are built specifically for mobile architectures and to enable portability.

PPG oximeters are medical monitoring devices that utilize PPG technology. PPG technology uses a noninvasive optical-based technique that measures the light absorption and refection properties of deoxygenated and oxygenated hemoglobin. The amount of light absorbed in the hemoglobin is defined by the Lambert-Beer Law, which associates the degree of light absorption with the wavelength of the beam light, the path length, and the absorption coefficient of the blood constituents. By illuminating a tissue bed with a light source and using a light-sensitive detector to measure the amount of light absorbed by the tissue, the concentration of oxygen in the arterial blood, heart rate, and blood flow can be estimated. The light source is typically a LED that shines visible red (650 nm) and infrared (IR) light (940 nm). The detector can be a photodetector (PD) configured to detect optical signals and convert them to electrical signals or pulses.

PPG technology can detect/measure optical signals in either a transmission mode or a reflectance (or reflective) mode. In the transmission mode, the PD is positioned opposite the LED light source to detect light that emanates from an illuminating surface of the LED and passes through the patient. A PPG oximeter that employs a transmission mode LED/PD configuration is limited to portions of the anatomy (e.g., the patient's finger or earlobes) that are thin enough for the LED light to pass through the body and be detected on the other side. In the reflective mode, the PD is positioned adjacent the LED light source to detect light that emanates from the illuminating surface of the LED, enters the patient, and is reflected from the patient's internal tissue back through the patient's skin. A PPG oximeter that employs a reflectance mode LED/PD configuration can detect reflected optical signals in any part of the human body where there is a reasonable concentration of blood vessels. The detected optical signals are converted to electrical signals that provide information on the proportion of the hemoglobin in the patient's blood that is dark red and deoxygenated versus bright red and oxygenated. By measuring how much of the LED light reaches the PD, the PPG oximeter can determine how much light has been absorbed because the amount of light absorbed is proportional to the length of the path that the light has to travel in the absorbing substance. The modulation of the oximeter signal with changes in the arterial diameter due to blood pressure variations in between heartbeats helps separate blood transmission characteristics from the unmodulated tissue background. In modern medical practice, the blood oxygen level is considered one of the important vital signs of the body, along with more traditional vital signs such as blood pressure, heart rate, body temperature, and breathing rate.

With the previously-described advances in low cost and small semiconductor components, low cost portable computing systems, and computer-based pulse wave analysis techniques, wearable healthcare sensors have been provided for continuously measuring a variety of health-related parameters, including, for example, blood pressure and electrocardiogram (ECG) measurements. However, providing a PPG oximeter in a wearable that performs continuous PPG-based monitoring without requiring any action by the wearer is a challenge because the strength of optical signals received at the PD is easily compromised when the wearer is moving around.

Turning now to an overview of aspects of the present invention, embodiments of the invention are directed to structures, computer-implemented methods, computer systems, and computer program products configured to provide a network of reflectance-mode PPG devices/sensors and a computing device housed in/on a wearable structure (e.g., a band). In accordance with aspects of the invention, signal strength detected by the network is improved and maintained even through the person wearing the wearable structure is moving around.

With respect to the structural aspects of the invention, each PPG device/sensor in the network can be formed from at least one light source and at least one detector. In embodiments of the invention, each PPG device/sensor in the network is formed from a red LED light source, an infrared (IR) LED light source, and a PD. Signal strength at the PD is improved by tilting the illuminating surfaces of one or more of the LEDs in the direction of the PD. In some embodiments of the invention, signal strength at the PD is further improved by tilting the detecting surface of the PD toward the LEDs. In embodiments of the invention, the illuminating and/or detecting surfaces of the LEDs and the PD are titled by an angle of about 3-5 degrees with respect to the skin surface. In embodiments of the invention, each PPG device/sensor is provide with a PPG device/sensor housing having sufficient rigidity to establish and maintain the LED and/or PD tilt when the housing is positioned on or directly over the skin. In some embodiments of the invention, the housing(s) are formed as an integral component of the wearable structure. In some embodiments of the invention, the housing(s) are formed as separate components that are attached to the wearable structure. In some embodiments of the invention, the wearable structure is formed from a more flexible material than the PPG device/sensor housings to improve comfort when the wearable structure is being worn by a user.

With respect to the computer-based aspects of the invention, embodiments of the invention provide computer-implemented methods, computer systems, and computer program products configured to analyze data about the environment in which the PPG device/sensor network is operating, along with data about the signal strength at each PPG device/sensor in the network in order to dynamically determine the PPG devices/sensors that are generating reliable output signals. Because the PPG device/sensor network is on a wearable structure, the positions of the PPG devices/sensors can change as the user moves around. Embodiments of the invention utilize machine learning algorithms to detect and rank the signal strength at each PPG device/sensor, generate a model of the network's environment, and map the ranked signal strength values to the model to dynamically determine the PPG devices/sensors in the network that are generating a reliable output. The network is controlled such that only the PPG devices/sensors that the network's computing device has determined are generating a reliable output are applied to the downstream PPG waveform analysis algorithms Eliminating the PPG devices/sensors that are not generating reliable output signals reduces computing power, improves computing speed, and improves the quality of the data provide to downstream PPG waveform analysis algorithms.

Turning now to a more detailed description of aspects of the invention, FIG. 1 depicts an example of a PPG device/sensor network 100 in accordance with embodiments of the present invention. The network 100 includes a computing device 130 and multiple individual PPG devices/sensors 112, configured and arranged as shown. For ease of illustration, six (6) individual PPG devices/sensors 112 are shown. However, the device/sensor network 100 can include any number of individual PPG devices/sensors 112 greater than two (2). The multiple PPG devices/sensors 112 are communicatively coupled, either wirelessly or through wires, to the computing device 130. The computing device 130 can be communicatively coupled, either wirelessly or through wires, through a network 140 to a remove server 150. The computing device 130 and the remote server 150 are depicted separately for ease of illustration and explanation. In embodiments of the invention, the functions described herein as being performed by the computing device 130 can be performed by the computing device 130 alone, distributed between the computing device 130 and the remote server 150, or performed by the remote server 150 alone.

Each PPG device/sensor 112 uses PPG technology to generate signals that measure a detected physical characteristic. In general, PPG technology is based on non-invasive optical measurements made at the skin surface to detect blood volume changes in the micro-vascular bed of tissue. Each PPG device/sensor 112 includes a light source (e.g., red LED 320 and/or infrared (IR) LED 330, shown in FIG. 3A) and a detector (e.g., photodiode (PD) 310 shown in FIG. 3A). In general, PPG devices/sensors operate in either a transmission mode or a reflective (or reflectance) mode. In the transmission mode, the possible measurement sites are limited in that the measurement must be taken at a portion of the anatomy that is thin enough for light to penetrate through it and be detected on the other side. Thus, transmission mode PPG optical measurements are typically taken at a finger, wherein the light source is on one skin surface of the finger, and the detector is placed on the opposite side of the same finger. In reflective-mode PPG technology, the measurement site can be almost anywhere because the light source transmits light into the body, and the detector detects portions of the transmitted light that have been back-scattered or reflected out of the body from tissue, bone and blood vessels.

The PPG devices/sensors 112 operate in the reflective mode to detect the changes in intensity of reflected light. The changes in light intensity are associated with small variations in blood perfusion of the tissue and provide information on the cardiovascular system, specifically, the pulse rate and the pulse wave. The principle behind the PPG technology used by the PPG devices/sensors 112 is the fact that light travelling though biological tissue can be absorbed by different substances, including pigments in the skin, bone, and arterial and venous blood. Most changes in blood flow occur mainly in the arteries and arterioles. Arteries contain more blood volume during the systolic phase of the cardiac cycle than during the diastolic phase. The PPG devices/sensors 112 optically detect changes in the blood flow volume (i.e., changes in the detected light intensity) in the micro-vascular bed of tissue via reflection of optical energy from the tissue.

The detector (e.g., PD 310 shown in FIG. 3A) of the PPG device/sensor 112 converts detected optical energy to a waveform that can provide valuable information about the cardiovascular system. PPG waveforms have a variety of useful characteristics, including but not limited to amplitude, periodicity, and time variance. PPG waveform amplitude is associated with anacrotic and dicrotic cardial periods that provide valuable data about vascular reaction process in reaction to short-duration factors. The periodicity of PPG waveforms represents data about cardiac cycle rate and heartbeat rate, as well as the correlation and time of systole, diastole, and its phases. For example, parameters such as time delay between anacrotic and diacrotic phases of the pulse wave, its period, pulse wave rising edge index, systole phase filling time, duration of systolic and diastolic phases, and heart rate can be measured. Additionally, known PPG waveform analysis algorithms can calculate various parameters from PPG waveform, including, for example, statistics showing the variability of amplitude and heart beat rate during long periods of time (minutes); dicrotic wave index; representations of the position of the dicrotic peak relatively to the anacrotic peak; the ratio of the anacrotic period to the dicrotic periods ratio. These and other calculated parameters allows medical professionals to diagnose instant body responses to environmental physical factors, as well as detect hemodynamics changes during long periods of time, thereby estimating the state of the cardiovascular system as a whole.

In accordance with aspects of the invention, the individual PPG devices/sensors 112 are configured and arranged to improve the strength of reflected optical signals detected by the individual PPG devices/sensors 112. In accordance with aspects of the invention, the computing device 130 is configured and arranged to utilize a variety of algorithms, including machine learning algorithms, configured to dynamically select the PPG devices/sensors 112 in the network 110 that will be used to generate the PPG waveform (s) from which physiological parameters will be derived. In embodiments of the invention, the computing device 130 selects PPG devices/sensors 112 based on a prediction that the strength of reflected optical signals detected by the PPG device/sensor 112 will exceed a predetermined/selected threshold of reliability. Specific details of the individual PPG devices/sensors 112 and the PPG device/sensor network 100 in accordance with aspects of the invention are depicted in FIGS. 2-10 and are described subsequently herein.

Figure 2:
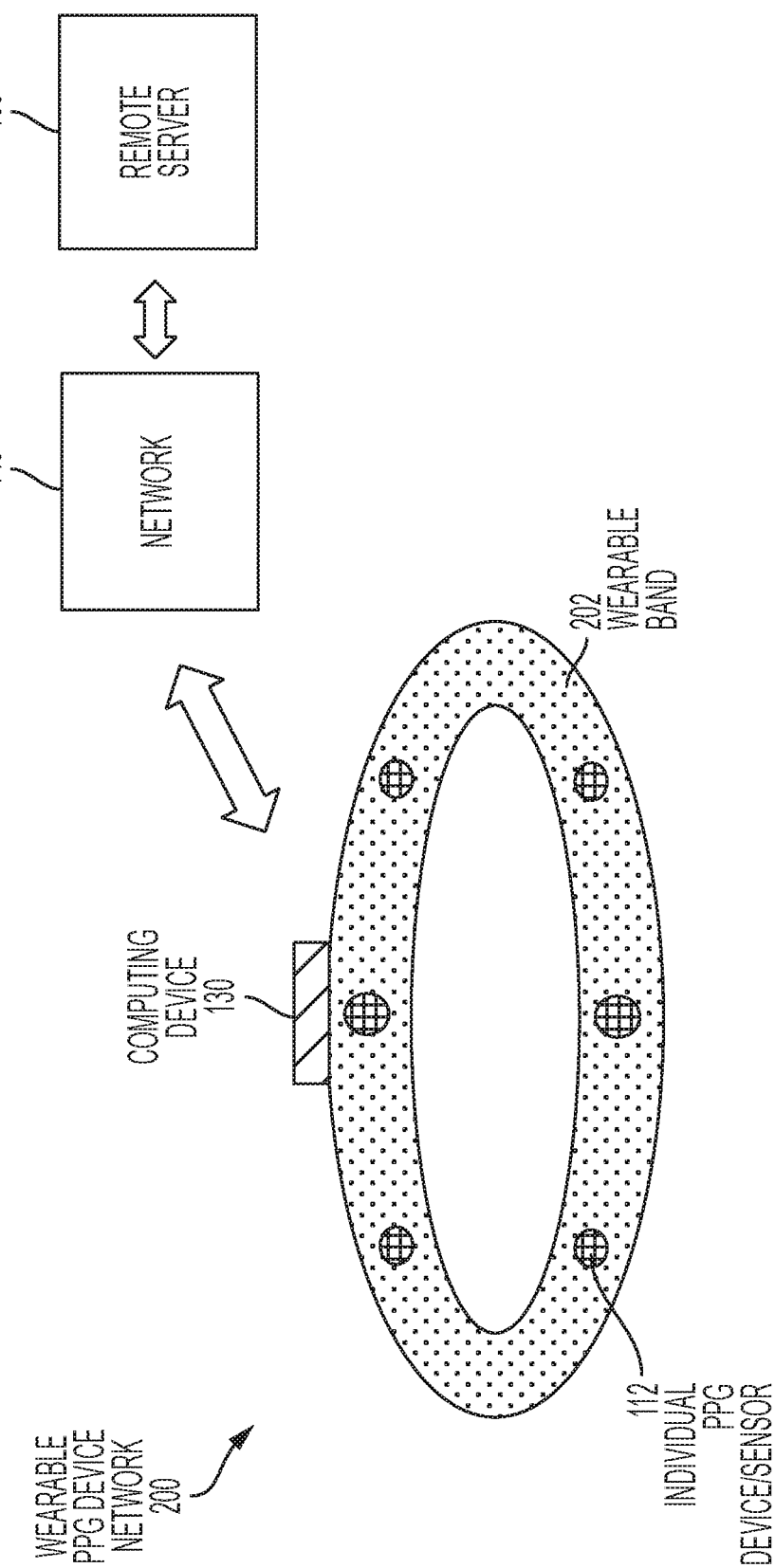
FIG. 2 is a block diagram of a wearable PPP device/sensor network in accordance with embodiments of the invention.

FIG. 2 is a block diagram of a wearable PPG device/sensor network 200 embodying aspects of the invention. In the embodiment of the invention depicted in FIG. 2, the wearable PPG device/sensor network 200 can be implemented by incorporating the PPG device/sensor network 100 (shown in FIG. 1) into a wearable band 202. The wearable band 202 can be flexible, rigid, or semi-rigid material configured to be worn around or on various parts of the body, including, for example, the ankle, wrist, chest, neck, biceps, forearms, and the like. The wearable band 202 can be dedicated to PPG monitoring, or the band 202 can include other functionality such as activity tracking, ECG measurement, smart watch functionality, and the like.

Figure 3A:
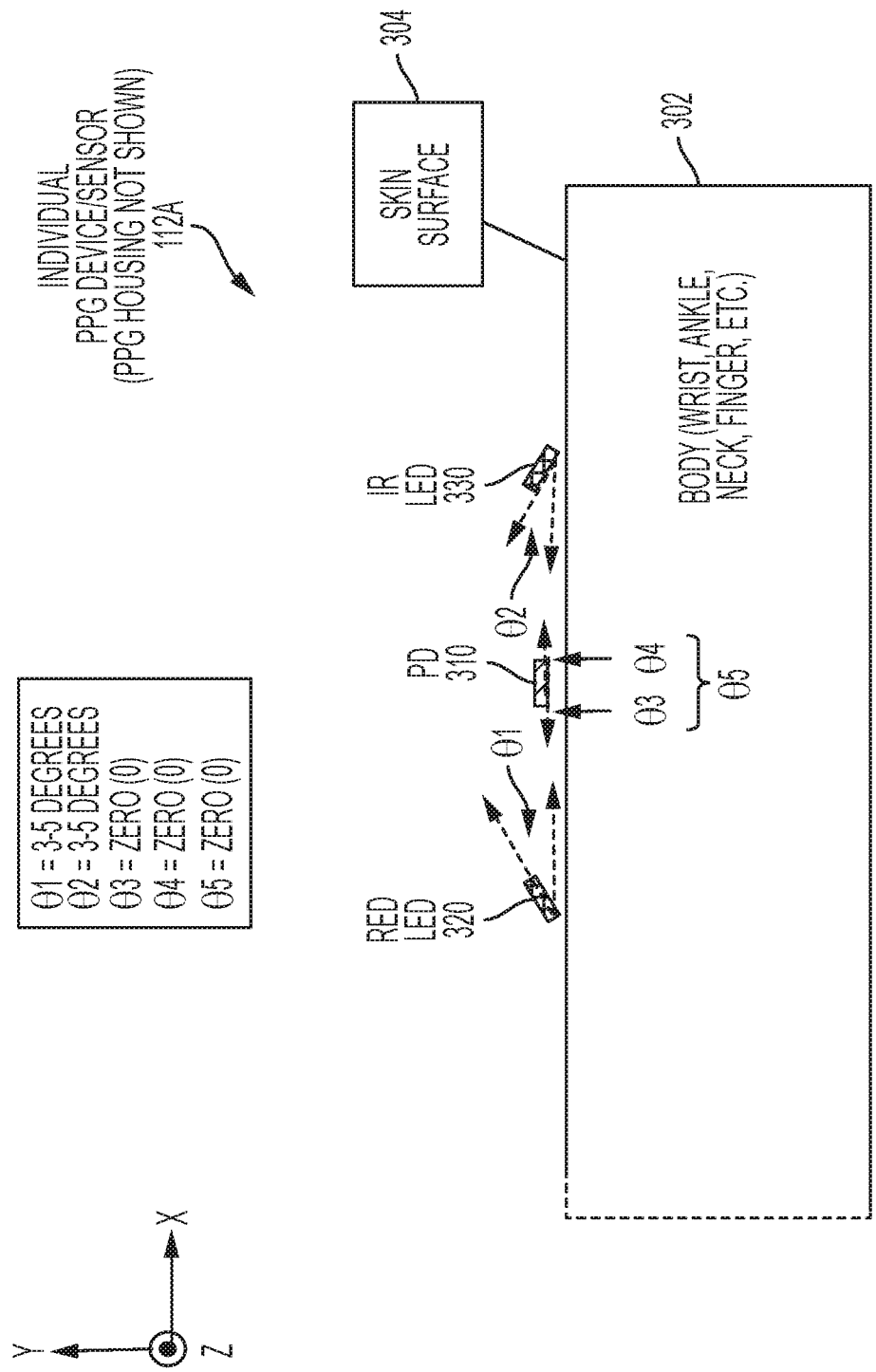
FIG. 3A is a block diagram illustrating details of an individual PPG device/sensor in accordance with embodiments of the invention.
Figure 3B:
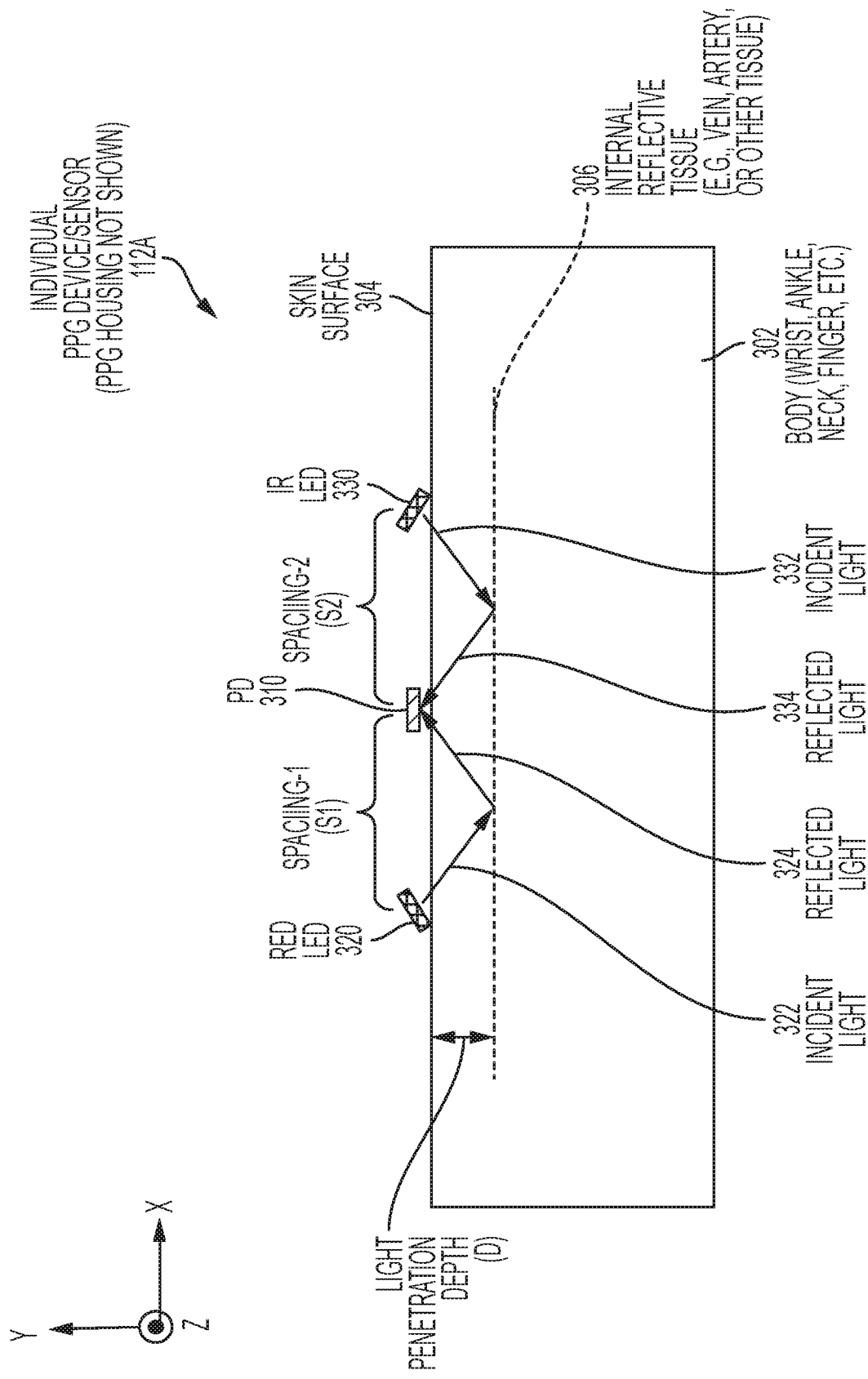
FIG. 3B is a block diagram illustrating details of an individual PPG device/sensor in accordance with embodiments of the invention.
Figure 3C:
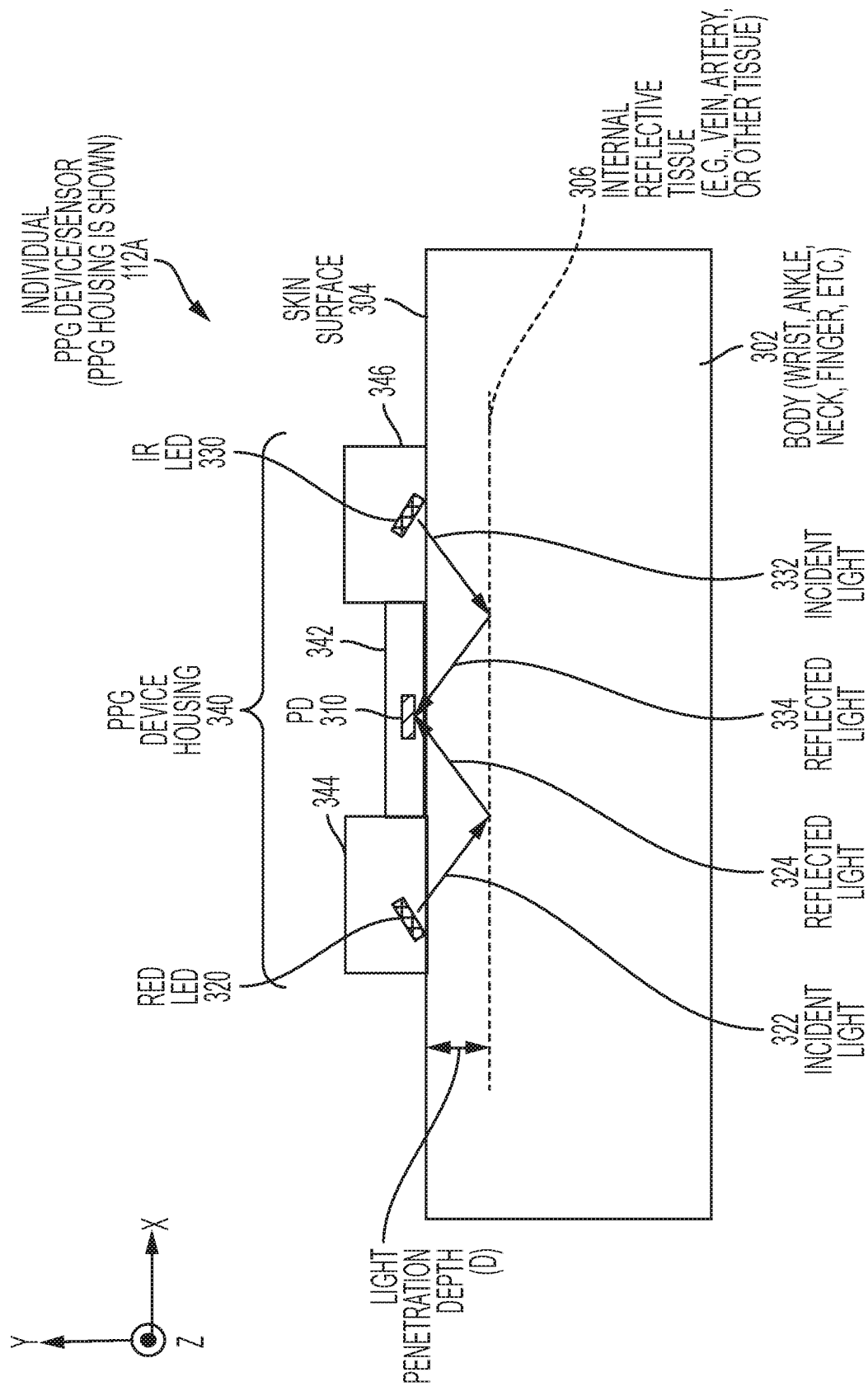
FIG. 3C is a block diagram illustrating details of an individual PPG device/sensor in accordance with embodiments of the invention.

FIGS. 3A, 3B, and 3C depict block diagrams illustrating various features of an individual PPG device/sensor 112A embodying aspects of the invention. In embodiments of the invention, the individual PPG device/sensor 112A shown in FIGS. 3A, 3B, and 3C can be deployed as the individual devices/sensors 112 of the PPG device/sensor network 100 (shown in FIG. 1) and of the wearable PPG device network 200 (shown in FIG. 2). FIG. 3A depicts the individual PPG device/sensor 112A without a PPG housing 340 (shown in FIG. 3A) in order to better illustrate the angles Θ1, Θ2, Θ3, Θ4, and Θ5 that are selected and maintained for the red LED 320, the IR LED 330, and the PD 310 of the individual PPG device/sensor 112A. FIG. 3B depicts the individual PPG device/sensor 112A without the PPG housing 340 in order to better illustrate the horizontal spacing S1 between the red LED 320 and the PD 310 of the individual PPG device/sensor 112A, as well as the horizontal spacing S2 between the PD 310 and the IR LED 330 of the individual PPG device/sensor 112A. FIG. 3C depicts the individual PPG device/sensor 112A with the red LED 320, the IR LED 330, and the PD 310 of the individual PPG device/sensor 112A secured in the PPG housing 340 in a manner that maintains the illuminating surfaces of the red LED 320 and the IR LED 330, as well as the detecting surfaces of the PD 310, at their respective angles Θ1, Θ2, Θ3, Θ4, and Θ5 when the housing 340 is positioned over/on the skin surface 340 of the body 302.

As shown in FIG. 3A, the red LED 320, the IR LED 330, and the PD 310 of the individual PPG device/sensor 112A are positioned over the surface skin 304 of a body 302. The red and IR LEDs 320, 330 are driven alternately with a precise current, and a quiet time occupies the interval between each alternating pulse. The repetition rate of the drive current is not fast, usually well under 10 kHz. The duty cycle is also kept low to keep overall power down and to allow ambient-light measurement while both LEDs 320, 330 are off. The PD 310 receives both ambient light and modulated light that originated from the red and IR LEDs 320, 330 then generates a current that will be measured over time to determine oxygen saturation. The current from the PD 310 can be converted to a voltage using an operational amplifier in a transimpedance configuration, also known as a transimpedance amplifier (TIA). The light received by the PD 310 is largely ambient light that is not useful for determining oxygen saturation or pulse. The small amount of red or IR infrared light not absorbed by the tissue, venous blood, or arterial blood is the signal of interest and is buried in the ambient light. Computer-based pulse wave analysis techniques are used to analyze the output from the PD 310 to isolate the signal of interest.

Because the optical signals of interest are a small part of the optical information received at the PD 310, the strength of the optical signals of interest is important. In accordance with aspects of the invention, the individual PPG device/sensor 112A is configured and arranged to improve the strength of reflected optical signals detected by the individual PPG device/sensor 112A operating in a reflective mode. In accordance with aspects of the invention, signal strength at the PD 310 is improved by positioning the red LED 320 and/or the IR LED 330 such that their illuminating surfaces are tilted toward the PD 310. In some embodiments of the invention, the PD 310 can be positioned such that its detecting surface is substantially parallel with respect to the skin's surface. In some embodiments of the invention, the PD 310 can be positioned such that its detecting surface is tilted toward the red LED 320 or the IR LED 330. In some embodiments of the invention, the PD 310 can include a segmented detection surface, wherein one portion of the segmented detecting surface is tilted toward the red LED 320, and wherein another portion of the segmented detection surface is tilted toward the IR LED 330. The inventors have determined that the strength of optical signals received at the PD of a reflectance-mode PPG oximeter is improved when the illuminating surface of the PPG oximeter's LED is tilted toward the PD at an angle from about 3-5 degrees with respect to the skin's surface while the PD's detecting surface remains substantially parallel with respect to the skin's surface. The inventors have also determined that the strength of optical signals received at the PD of a reflectance-mode PPG oximeter is improved when the illuminating surface of the PPG oximeter's LED is tilted toward the PD at an angle from about 3-5 degrees with respect to the skin's surface while the detecting surface of the PD is tilted toward the LED at an angle from about 3-5 degrees with respect to the skin's surface.

The various tilts of the red LED 320, the IR LED 330, and the PD 310 are represented in FIG. 3A by the angles Θ1, Θ2, Θ3, Θ4, and Θ5. The angle Θ1 represents the upward tilt angle of the illuminating surface of the RED LED 320 with respect to the skin surface 304 (i.e., the x-axis). The angle Θ2 represents the upward tilt angle of the illuminating surface of the IR LED 330 with respect to the skin surface 304 (i.e., the x-axis). The angle Θ5 assumes that the detecting surface of the PD 310 is substantially unitary and not segmented. Accordingly, the angle Θ5 represents the tilt angle of the unitary detecting surface of the IR LED 330 with respect to the skin surface 304 (i.e., the x-axis). The angle Θ3 assumes that the detecting surface of the PD 310 is segmented and not substantially unitary. Accordingly, the angle Θ3 represents the upward tilt angle of one of the segmented detecting surfaces of the IR LED 330 with respect to the skin surface 304 (i.e., the x-axis). The angle Θ4 assumes that the detecting surface of the PD 310 is segmented and not substantially unitary. Accordingly, the angle Θ4 represents the upward tilt angle of one of the segmented detecting surfaces of the IR LED 330 with respect to the skin surface 304 (i.e., the x-axis). In the example depicted in FIG. 3A, the detecting surface (both unitary and segmented) of the PD 310 is substantially parallel with respect to the skin surface 304PD 310, and the illuminating surfaces of the RED LED 320 and the IR LED 330 are both tilted upward and toward the PD 310. Accordingly, in the example depicted in FIG. 3A, Θ1 is from about 3-5 degrees with respect to the skin surface 304, Θ2 is from about 3-5 degrees with respect to the skin surface 304, and Θ5 is about zero (0) degrees with respect to the skin surface 304.

Other combinations of values are contemplated for the angles Θ1, Θ2, Θ3, Θ4, and Θ5. In embodiments of the invention, the detecting surface of the PD 310 is segmented, one of the segmented detecting surfaces of the PD 310 is tilted upward toward the RED LED 320, one of the segmented detecting surfaces of the PD 310 is substantially parallel with respect to the skin surface 304, and the illuminating surfaces of the RED LED 320 and the IR LED 330 are both tilted upward and toward the PD 310. Accordingly, in this example, Θ1 is from about 3-5 degrees with respect to the skin surface 304, Θ2 is from about 3-5 degrees with respect to the skin surface 304, Θ3 is from about 3-5 degrees with respect to the skin surface 304, and Θ4 is about zero (0) degrees with respect to the skin surface 304. In embodiments of the invention, the detecting surface of the PD 310 is segmented, one of the segmented detecting surfaces of the PD 310 is tilted upward toward the IR LED 330, one of the segmented detecting surfaces of the PD 310 is substantially parallel with respect to the skin surface 304, and the illuminating surfaces of the RED LED 320 and the IR LED 330 are both tilted upward and toward the PD 310. Accordingly, in this example, Θ1 is from about 3-5 degrees with respect to the skin surface 304, Θ2 is from about 3-5 degrees with respect to the skin surface 304, Θ3 is about zero (0) degrees with respect to the skin surface 304, and Θ4 is from about 3-5 degrees with respect to the skin surface 304. In embodiments of the invention, the detecting surface of the PD 310 is segmented, one of the segmented detecting surfaces of the PD 310 is tilted upward toward the RED 320, one of the segmented detecting surfaces of the PD 310 is tilted upward toward the IR LED 330, and the illuminating surfaces of the RED LED 320 and the IR LED 330 are both tilted upward and toward the PD 310. Accordingly, in this example, Θ1 is from about 3-5 degrees with respect to the skin surface 304, Θ2 is from about 3-5 degrees with respect to the skin surface 304, Θ3 is about 3-5 degrees with respect to the skin surface 304, and Θ4 is from about 3-5 degrees with respect to the skin surface 304.

FIG. 3B depicts the individual PPG device/sensor 112A without the PPG housing 340 (shown in FIG. 3C) in order to better illustrate an example path of incident light 322, 332 passing from the illuminating surfaces of the red and IR LEDs 320, 330 through the skin surface 304 such that the incident light hits internal reflective tissue (or bone, etc.) 306 and is reflected as reflected light 324, 334 to the detecting surface of the PD 340. As shown in FIG. 3B, the red LED 320, the IR LED 330, and the PD 310 of the individual PPG device/sensor 112A are positioned over the surface skin 304 of the body 302. In accordance with aspects of the invention, the red LED 320 and the IR LED 330 are positioned such that their illuminating surfaces are each tilted toward the PD 310. The light output from the red and IR LEDs 320, 330 has an illumination pattern. For example, the red and IR LEDs 320, 330 can generate an illumination pattern having a divergence of 38 degrees in the x-axis direction and 47 degrees in the y-axis direction. Signal strength is strongest toward the middle of the illumination pattern and dissipates toward the edges of the illumination pattern. By tilting the illuminating surfaces of the LEDs 320, 330 toward the PD 310, and/or by tilting the detecting surface of the PD 310 toward the illuminating surfaces of the LEDs 320, 330, more light from the middle of the illumination patterns of the LEDs 320, 330 will be reflected to the detecting surface of the PD 310, thereby improving the strength of the signals of interest (red and IR light) received at the PD 310.

In aspects of the invention, each of the LED light sources 320, 330 can be configured as a two-lead semiconductor-based p-n junction diode that emits light when activated by current. When a suitable current is applied to the leads, electrons are able to recombine with electron-holes within the diode, thereby releasing energy. The recombined electrons dissipate energy in the form of heat for silicon (Si) and germanium (Ge) diodes, but in gallium arsenide phosphide (GaAsP) and gallium phosphide (GaP) semiconductors, the electrons dissipate energy by emitting photons. If the semiconductor is translucent, the junction becomes the source of light as it is emitted, thus becoming a light-emitting diode. This effect is called electroluminescence, and the color of the light (corresponding to the energy of the photon) is determined by the energy band gap of the semiconductor. LEDs of type used in PPG technology are typically small (less than 1 mm$^2$). Although some LED applications utilize optical components to shape the radiation pattern of the LED, such optical components are not used in PPG oximeters. In PPG oximeters, the LED light source can be configured as a flat-surface uncoated simple square LED with substantially 90-degree angled surfaces on all sides. The LED light source emits light substantially perpendicular to the semiconductor's illuminating surface and a few degrees to the side, thereby emanating light in a cone-shape referred to as the light cone, the cone of light, the escape cone, or the illumination pattern. The maximum angle of incidence is referred to as the critical angle. When the critical angle is exceeded, photons no longer escape the semiconductor but are, instead, reflected internally inside the LED semiconductor crystal as if it were a mirror. Internal reflections can escape through other crystalline faces if the incidence angle is low enough and the crystal is sufficiently transparent to not re-absorb the photon emission. However, for a simple square LED with 90-degree angled surfaces on all sides, the faces all act as equal angle mirrors. In this case, most of the internally reflected light cannot escape and is lost as waste heat in the LED crystal.

In some embodiments of the invention, the semiconductor chip that forms the LEDs 320, 330 can be encapsulated or potted in clear or colored molded solid plastic. The plastic encapsulation can facilitate mounting the semiconductor chip to form an LED device. Additionally, encapsulation can physically support and protect from damage the small and fragile electrical wiring used by the semiconductor chip. The encapsulation can also act as a refractive intermediary between the relatively high-index semiconductor and low-index open air. The encapsulation can also be configured to boost the light emission from the semiconductor by acting as a diffusing lens, emitting light at a much higher angle of incidence from the light cone than the bare semiconductor chip would alone. In embodiments of the invention, the illuminating surface, which is substantially planar, can be a surface of the semiconductor chip or a surface of the encapsulation.

In accordance with aspects of the invention, the PD 310 can be formed in the same manner as the LEDs 320, 330 except the PD semiconductor chip and p-n junction thereof are configured to operate in a reverse bias such that the PD semiconductor chip absorbs light and converts the absorbed light to a proportional current. In some aspects of the invention, a diode configured for use as the PD 310 can use a PIN junction rather than a p-n junction to increase the speed of response.

FIG. 3B also depicts the individual PPG device/sensor 112A without the PPG housing 340 (shown in FIG. 3C) in order to better illustrate the horizontal spacing S1 between the red LED 320 and the PD 310, as well as the horizontal spacing S2 between the PD 310 and the IR LED 330. In known pulse oximeters, the spacings between the PD and the red and IR LEDs are selected based on a variety of design considerations including, for example, the estimated light penetration depth(s) (D) and the illumination patterns of the red and IR LEDs. In embodiments of the invention, the spacings S1 and S2 take into account the above-described design considerations (and others), along with the additional consideration of the tilts defined by the angles Θ1, Θ2, Θ3, Θ4, and Θ5. The final determination of S1 and S2 is selected to not compromise the improved signal strength generated by the angles Θ1, Θ2, Θ3, Θ4, and Θ5. In some embodiments of the invention, the selection of S1 and S2 values that do not compromise the improved signal strength generated by the angles $\Theta1$, $\Theta2$, $\Theta3$, $\Theta4$, and $\Theta5$ can be determined through experimentation and/or geometry-based calculations.

FIG. 3C depicts the individual PPG device/sensor 112A with the red LED 320, the IR LED 330, and the PD 310 secured in the PPG housing 340 in a manner that maintains the red LED 320, the IR LED 330, and the PD 310 at their respective angles $\Theta1$, $\Theta2$, $\Theta3$, $\Theta4$, and $\Theta5$ when the housing 340 is positioned over/on the skin surface 304. The housing 340 can take a variety of forms and be made from a variety of materials. In accordance with aspects of the invention, a characteristic of the housing 340 is that it is formed from a material having sufficient rigidity that it maintains the red LED 320, the IR LED 330, and the PD 310 at their respective angles $\Theta1$, $\Theta2$, $\Theta3$, $\Theta4$, and $\Theta5$ when the housing 340 is on/over the skin surface 304. In accordance with aspects of the invention, another characteristic of the housing 340 is that it is formed from a material having light transmission characteristics such that, when the red LED 320, the IR LED 330, and the PD 310 are mounted therein at their respective angles $\Theta1$, $\Theta2$, $\Theta3$, $\Theta4$, and $\Theta5$, light emanating from the illuminating surfaces of the LEDs 320, 330 and light reflected to the PD 310 passes through the housing 340. In some embodiments of the invention, the LEDs 320, 330 and the PD 310 can be mounted in the housing 340 such that the illuminating and/or detecting surfaces of the LEDs 320, 330 and the PD 310 are exposed and do not need to pass through the housing 340. In the example shown in FIG. 3B, the housing 340 includes three segments 342, 344, 346. Housing segment 342 is configured to secure the PD 310 at its angle(s) $\Theta3$, $\Theta4$, $\Theta5$ when the housing 340 is positioned over/on the skin surface 304. Housing segment 344 is configured to secure the red LED 320 at its angle $\Theta1$ when the housing 340 is positioned over/on the skin surface 304. Housing segment 346 is configured to secure the IR LED 330 at its angle $\Theta2$ when the housing 340 is positioned over/on the skin surface 304. The housing 340 can be formed integral to the wearable band 202 (shown in FIG. 2) or can be a separate structure attached to the wearable band 202. In some embodiments of the invention, the band 202 can be formed from more flexible material than the housing 340 to improve comfort for the user. In some embodiments of the invention, the individual PPG device/sensor 112A can be fabricated using three-dimensional (3D) printing.

Figure 4:
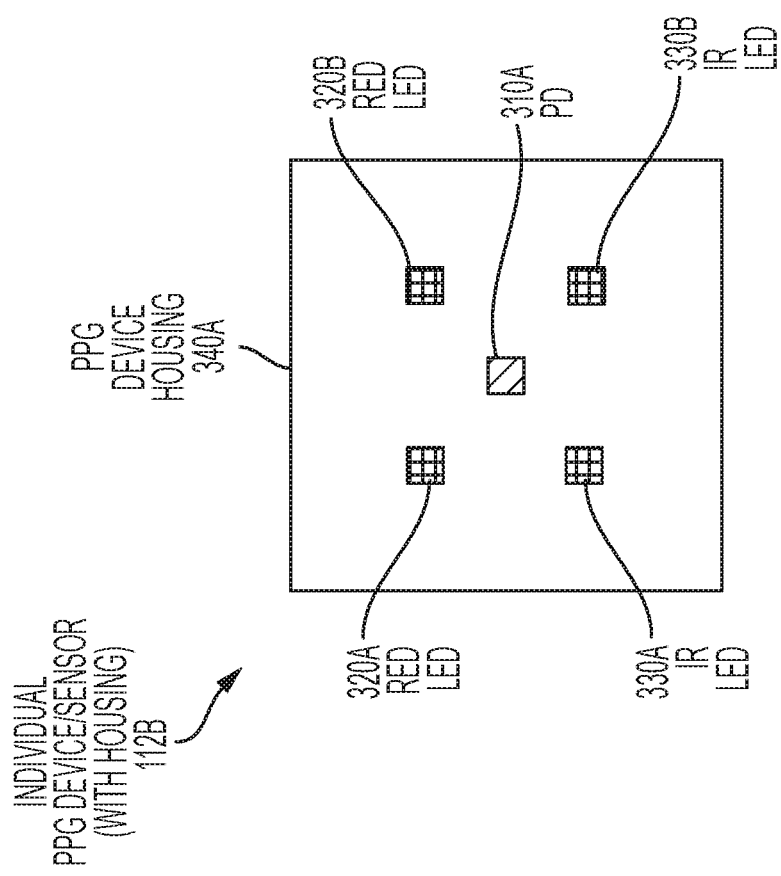
FIG. 4 is a block diagram illustrating details of an individual PPG device/sensor in accordance with embodiments of the invention.

FIG. 4 is a block diagram illustrating a side-view of an individual PPG device/sensor 112B having multiple instances of the red LED 320A, 320B and multiple instances of the IR LED 330A, 330B according to aspects of the invention. Although four (4) LEDS and one (1) PD are depicted in FIG. 4, more than four (4) LEDs and one (1) PD can be provided. The multiple LEDs 320A, 320B, 330A, 330B of the individual PPG device/sensor 112B are configured to generate a larger amount of incident light than the individual PPG device/sensor 112A (shown in FIGS. 3A, 3B, and 3C), thereby receiving a larger amount of reflected light at the PD 310A than the PD 310 (shown in FIGS. 3A, 3B, 3C). The individual PPG device/sensor 112B is supported in a housing 340A. Similar to the individual PPG device/sensor 112A (shown in FIGS. 3A, 3B, 3C), the LEDs 320A, 320B, 320C, 320D are positioned within the housing 340A such that the illuminating surfaces of the LEDs 320A, 320B, 330A, 330B are tilted upward toward the PD 310A when the housing 340A is positioned on/over the skin surface (e.g., skin surface 304 shown in FIGS. 3A, 3B, 3C). In some embodiments of the invention, the PD 310A is positioned within the housing 340A such that the detecting surface of the PD 310A is substantially parallel with the skin surface (e.g., skin surface 304 shown in FIGS. 3A, 3B, 3C) when the housing 340A is positioned on/over the skin surface (e.g., skin surface 304 shown in FIGS. 3A, 3B, 3C). In some embodiments of the invention, when the housing 340A is positioned on/over the skin surface (e.g., skin surface 304 shown in FIGS. 3A, 3B, 3C), the PD 310A can include a segmented detection surface, wherein when one portion of the segmented detecting surface is tilted toward the red LEDs 320A, 320B, and wherein another portion of the segmented detection surface is tilted toward the IR LEDs 330A, 330B. In some embodiments of the invention, when the housing 340A is positioned on/over the skin surface (e.g., skin surface 304 shown in FIGS. 3A, 3B, 3C), the PD 310A can include a segmented detection surface, wherein when one portion of the segmented detecting surface is tilted toward the red LED 320A, wherein when another portion of the segmented detecting surface is tilted toward the red LED 320B, wherein another portion of the segmented detection surface is tilted toward the IR LED 330A, and wherein another portion of the segmented detection surface is tilted toward the IR LED 330B. The respective angles $\Theta1$, $\Theta2$, $\Theta3$, $\Theta4$, and $\Theta5$ shown in FIG. 3A apply equally to the individual PPG device/sensor 112B with appropriate adjustments for the additional LEDs 320B, 330B.

The individual PPG device/sensor 112B is secured in the housing 340A in a manner that maintains the red LEDs 320A, 320B, the IR LEDs 330A, 330B, and the PD 310A at their respective tilted angles when the housing 340A is positioned over/on the skin surface 304 (shown in FIGS. 3A, 3B, 3C). The housing 340A can take a variety of forms and be made from a variety of materials. In accordance with aspects of the invention, a characteristic of the housing 340A is that it maintains the red LEDs 320A, 320B, the IR LEDs 330A, 330B and the PD 310A at their respective tilted angles when the housing 340A is on/over the skin surface 304. In accordance with aspects of the invention, another characteristic of the housing 340A is that it is formed from a material having light transmission characteristics such that, when the red LEDs 320A, 320B, the IR LEDs 330A, 330B, and the PD 310A are mounted therein at their respective angles $\Theta1$, $\Theta2$, $\Theta3$, $\Theta4$, and $\Theta5$, light emanating from the illuminating surfaces of the LEDs 320A, 320B, 330A, 330B and light reflected to the PD 310A pass through the housing 340A. In some embodiments of the invention, the LEDs 320A, 320B, 330A, 330B and the PD 310A can be mounted in the housing 340 such that the illuminating and/or detecting surfaces of the LEDs 320A, 320B, 330A, 330B and the PD 310A are exposed and do not need to pass through the housing 340A. The housing 340A can be formed integral to the wearable band 202 (shown in FIG. 2) or can be a separate structure attached to the wearable band 202. In some embodiments of the invention, the individual PPG device/sensor 112B can be fabricated using three-dimensional (3D) printing.

Figure 5:
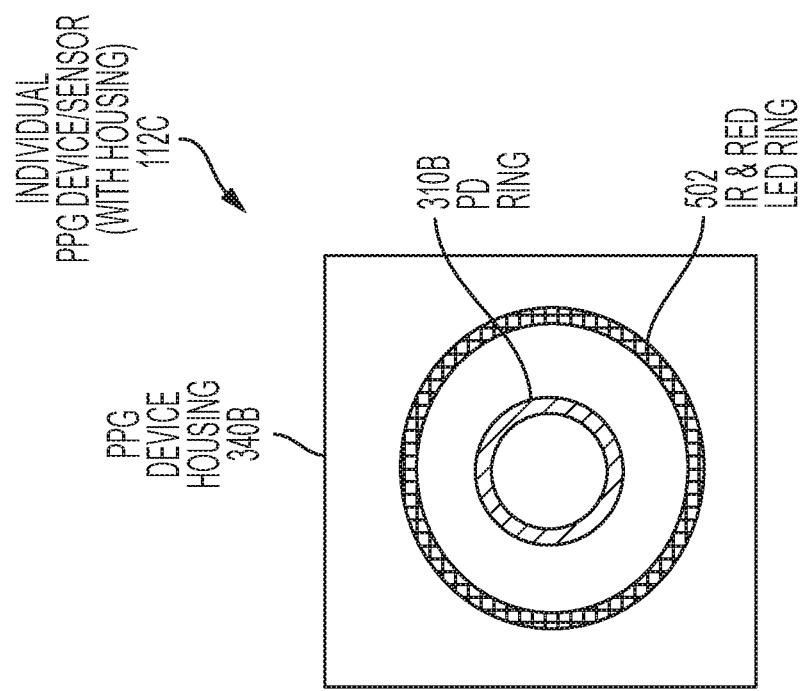
FIG. 5 is a block diagram illustrating details of an individual PPG device/sensor in accordance with embodiments of the invention.

FIG. 5 is a block diagram illustrating a side-view of an individual PPG device/sensor 112C having multiple instances of the previously described red LEDs and IR LEDs formed in a ring 502, along with multiple instances (or a single unitary instance) of the previously described PDs formed in a ring 310B according to aspects of the invention. In some aspects of the invention, the individual PPG device/sensor 112C can have a single curved instance of the previously described red LED and a single curved instance of the IR LED, both of which are formed as the ring 502. The ring of LEDs 502 of the individual PPG device/sensor 112C is configured to generate a larger amount of incident light than the individual PPG device/sensor 112A (shown in FIGS. 3A, 3B, and 3C), thereby receiving a larger amount of reflected light at the ring of PDs 310B than the PD 310 (shown in FIGS. 3A, 3B, 3C). The individual PPG device/sensor 112C is supported in a housing 340B. Similar to the individual PPG device/sensor 112A (shown in FIGS. 3A, 3B, 3C), the illuminating surfaces of the ring of LEDs 502 are tilted toward the ring of PDs 310B when the housing 340B is positioned on/over the skin surface (e.g., skin surface 304 shown in FIGS. 3A, 3B, 3C). In some embodiments of the invention, the detecting surfaces of the ring of PDs 310B are tilted toward the ring of PDs 310B when the housing 340B is positioned on/over the skin surface (e.g., skin surface 304 shown in FIGS. 3A, 3B, 3C). The respective angles Θ1, Θ2, Θ3, Θ4, and Θ5 shown in FIG. 3A apply equally to the individual PPG device/sensor 112B with appropriate adjustments for the additional LEDs in the ring 502 and the additional PDs in the ring 310B.

The individual PPG device/sensor 112C is secured in the housing 340B in a manner that maintains the ring of LEDs 502 and the ring of PDs 310B at their respective tilted angles when the housing 340B is positioned over/on the skin surface 304 (shown in FIGS. 3A, 3B, 3C). The housing 340B can take a variety of forms and be made from a variety of materials. The important characteristics of the housing 340B is that it maintains the ring of LEDs 502 and the ring of PDs 310B at their respective tilted angles when the housing 340B is on/over the skin surface 304. The housing 340B can be formed integral to the wearable band 202 (shown in FIG. 2) or can be a separate structure attached to the wearable band 202. In some embodiments of the invention, the individual PPG device/sensor 112C can be fabricated using three-dimensional (3D) printing.

Figure 6:
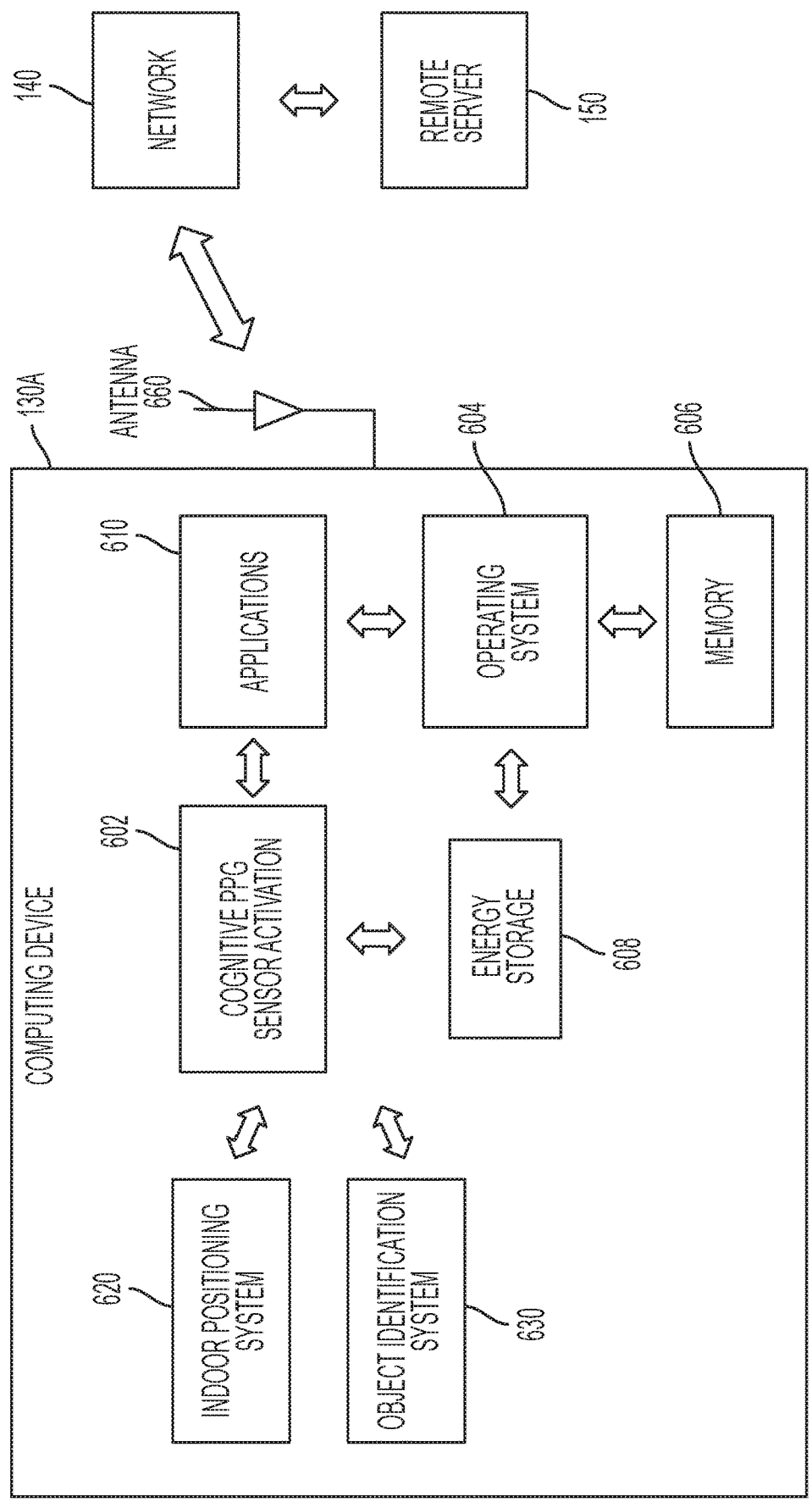
FIG. 6 is a block diagram illustrating details of a computing device in accordance with embodiments of the invention.

FIG. 6 is a block diagram illustrating details of a computing device 130A embodying aspects of the invention. The computing device 130A is a more detailed implementation of the computing device 130 (shown in FIGS. 1 and 2). As previously described herein, in accordance with aspects of the invention, the individual PPG devices/sensors 112, 112A, 112B, 112C (shown in FIGS. 1-3C) are configured and arranged to improve the strength of reflected optical signals detected by the PDs 310, 310A, 310B (shown in FIGS. 2-3C) by tilting the LEDs 320, 320A, 320B, 330, 330A, 330C (shown in FIGS. 2-3C) and/or the PDs 310, 310A, 310B. In accordance with additional aspects of the invention, the computing device 130A is configured and arranged to utilize a variety of algorithms, including machine learning (ML) algorithms (e.g., ML algorithms 702 shown in FIG. 7) configured to dynamically select the PPG devices/sensors 112, 112A, 112B, 112C that will be used to generate the PPG waveform(s) from which the computing device 130A will derive physiological parameters. In embodiments of the invention, the computing device 130A selects PPG devices/sensors 112, 112A, 112B, 112C based on a prediction that the strength of reflected optical signals detected by the selected ones of the PPG devices/sensors 112, 112A, 112B, 112C will exceed a threshold. Specific details of how the computing device 130A operates are depicted in FIGS. 6-10 and described subsequently herein.

The computing device 130A is configured to communicate through an antenna 660 with a network 140 and a remove server 150. The computing device 130A includes an operating system 604, a memory 606, energy storage (e.g., a rechargeable battery) 608, applications 610, a cognitive PPG sensor activation module 602, an indoor positioning system 620, and an object identification system 630, configured and arranged as shown. The various components/modules of the computing device 130A are depicted separately for ease of illustration and explanation. In embodiments of the invention, the functions performed by the various components/modules of the computing device 130A can be distributed differently than shown. For example, some or all of the functionality of the indoor positioning system 620 could be integrated with some or all of the functionality of the object detection system 630. Additionally, the bidirectional arrows between the operating system 604, the memory 606, the energy storage 608, the applications 610, the cognitive PPG sensor activation module 602, the indoor positioning system 610, and the object identification system 630 are provided to indicate that data, controls and other signals can be passed through a variety of paths between any of the components of the computing device 130A.

In embodiment of the invention, the illustrated components of the computing device 130A can be implemented as one or more modules. Embodiments of the present invention apply to a wide variety of module implementations. For example, a module can be implemented as a hardware circuit including custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like. Modules can also be implemented in software for execution by various types of processors. An identified module of executable code can, for instance, include one or more physical or logical blocks of computer instructions which can, for instance, be organized as an object, procedure, or function. Nevertheless, the executables of an identified module need not be physically located together, but can include disparate instructions stored in different locations which, when joined logically together, form the module and achieve the stated purpose for the module.

In accordance with aspects of the invention, the applications 610 are various types of application programming instructions configured to implement various types of functionality of the computing device 130A. For example, the applications 610 can include computer-based pulse wave analysis techniques for processing and analyzing electrical signals output from the PDs 310, 310A, 310B (shown in FIGS. 3A-3C). The applications 610 can be stored in the memory 606. The operating system 604 includes an interpreter (not shown) that interprets and executes the various programming instructions that form the applications 610. The energy storage 608 provides electric power to the various components/modules of the computing device 130A and can be implemented as a rechargeable battery.

The indoor positioning system 620 includes the various positioning-enabled sensors such as GPS receivers, accelerometers, gyroscopes, digital compasses, cameras, Wi-Fi etc. that have been built into the computing device 130A to determine the location and movements of the computing device 130A and the wearable band 202 (shown in FIG. 2) on which the computing device 130A is mounted. The indoor positioning system 620 can also be described as a hybrid positioning system that relies on several different positioning technologies, including, for example, GPS, cell tower signals, wireless internet signals, Bluetooth sensors, IP addresses, and network environment data. These systems are specifically designed to overcome the limitations of GPS, which is very exact in open areas, but works poorly indoors or between tall buildings (the urban canyon effect).

By comparison, cell tower signals are not hindered by buildings or bad weather, but usually provide less precise positioning. Wi-Fi positioning systems can give very exact positioning, in urban areas with high Wi-Fi density but depend on a comprehensive database of Wi-Fi access points.

The object identification system 630 can be implemented using a variety of technologies including image-based and/or acoustic-based object identification technologies. Image-based object identification can rely on a camera system of the computing device 130A, along with image processing algorithms to identify the objects in the image. Acoustic-based object identification can be implemented as, for example, an acoustic pulse-echo system that include a source of ultrasonic energy, an ultrasonic transducer coupled to the source for emitting a narrow pulse or series of pulses of ultrasonic energy, a second ultrasonic transducer for receiving return pulses from objects within a predetermined detection zone, and a detection circuit coupled to the ultrasonic transducer for providing output signals when a predetermined criterion is met by the return pulses. The output signals can be analyzed by known algorithms to generally identify classes of objects. For example, in accordance with aspects of the invention, the algorithms can be configured to identify the position of a person wearing the band 202 (shown in FIG. 2) with respect to the band 202 to conclude whether any part of the band is currently resting on the person (e.g., the person's wrist) and what part of the band 202 (e.g., a portion of the band 202 that houses an individual PPG device/sensor 112, 112A, 112B, 112C (shown in FIGS. 2-3C) is resting on the person.

The cognitive PPG sensor activation module 602 is configured and arranged to control whether or not the signal from one of the PPG devices/sensors 112 (shown in FIGS. 1 and 2) will be provided to and analyzed by the applications 610. In accordance with aspects of the invention, a model of the environment in which the computing device 130A is located is generated. More specifically, in accordance with aspects of the invention, the model of the environment in which the computing device 130A is located includes whether a PPG device/sensor 112 of the band 202 is resting on the user. This model is referred to herein as the PPG signal strength model. As an example, the PPG signal strength model can determine that the computing device 130A is mounted on the band 202 (shown in FIGS. 1 and 2), which is being worn by a user who is walking down the street with his/her arms swinging back and forth. The PPG signal strength model can further determine that, while the person is walking in this manner and at this pace, two of the PPG devices/sensors 112 will never rest sufficiently on the person's wrist to obtain a sufficient signal therefrom. The PPG signal strength model can further determine that, while the person is walking in this manner and at this pace, two of the PPG devices/sensors 112 will rest sufficiently on the person's wrist to obtain a sufficient signal therefrom only during a time when the person's arm is swinging forward. The PPG signal strength model can further determine that, while the person is walking in this manner and at this pace, two of the PPG devices/sensors 112 will rest sufficiently on the person's wrist to obtain a sufficient signal therefrom only during a time when the person's arm is swinging backward. In this example, the computing device 130A (and specifically, the cognitive PPG sensor activation module 602 and the ML algorithms 702) would only allow signals to be read and processed from the PPG devices/sensors 112 that the PPG signal strength model determines is or will be positioned on the user. The PPG signal strength model can be generated by the cognitive PPG sensor activation module 602 classifying training data and identifying and/or mapping relationships between and among the classified training data.

Figure 7:
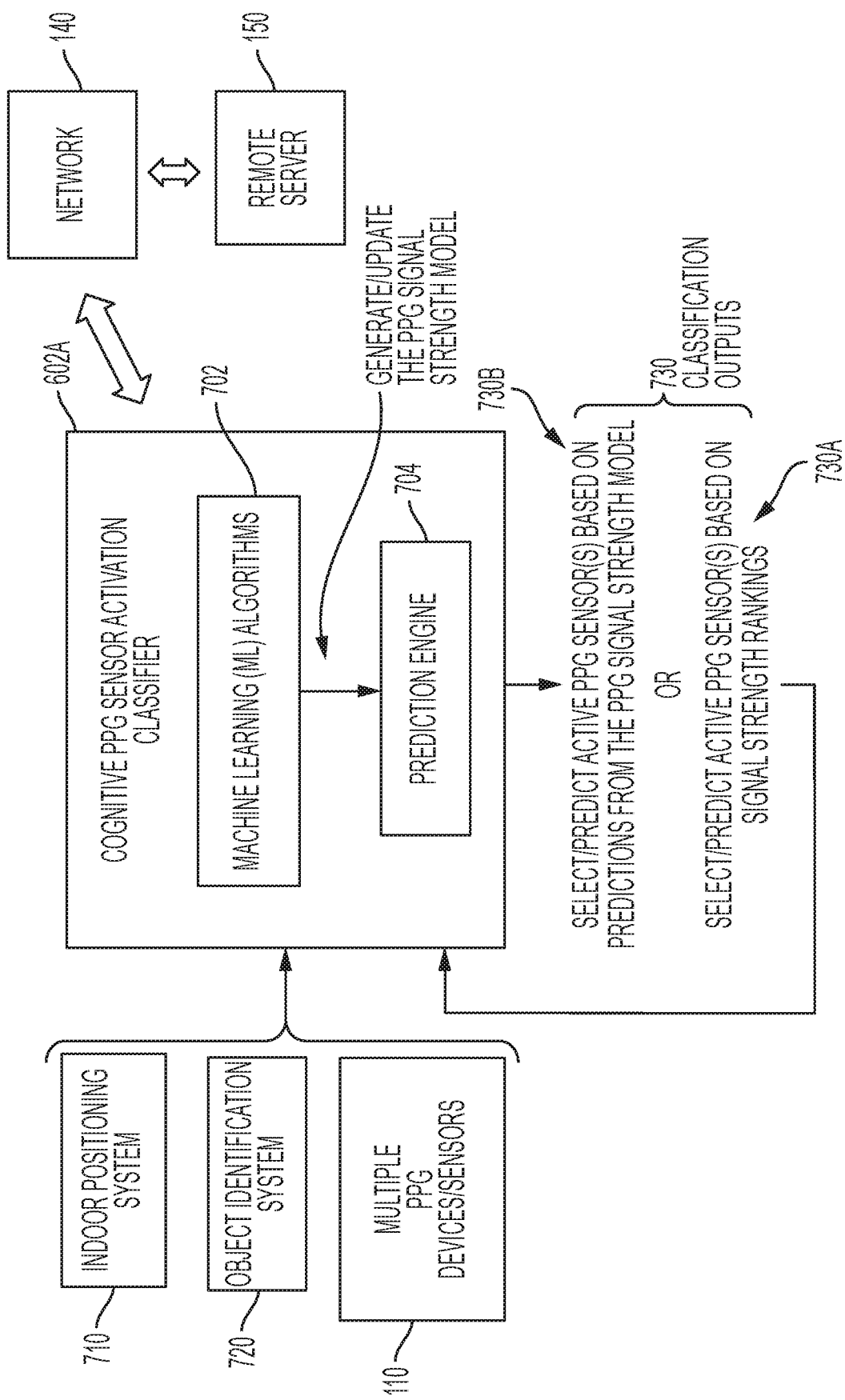
FIG. 7 is a block diagram illustrating details of a cognitive PPG device/sensor activation classifier in accordance with embodiments of the invention.
Figure 8A:
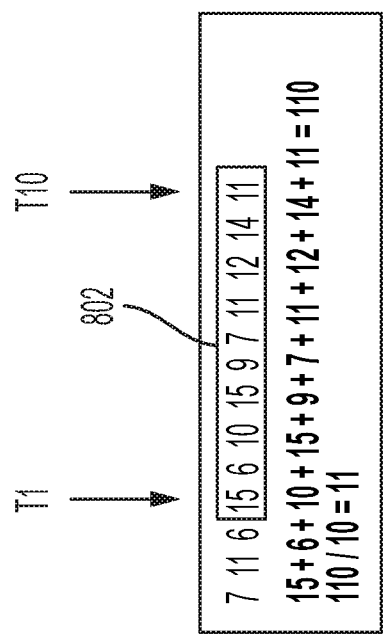
FIG. 8A is a block diagram illustrating a moving average signal strength analysis method in accordance with embodiments of the invention.
Figure 8B:
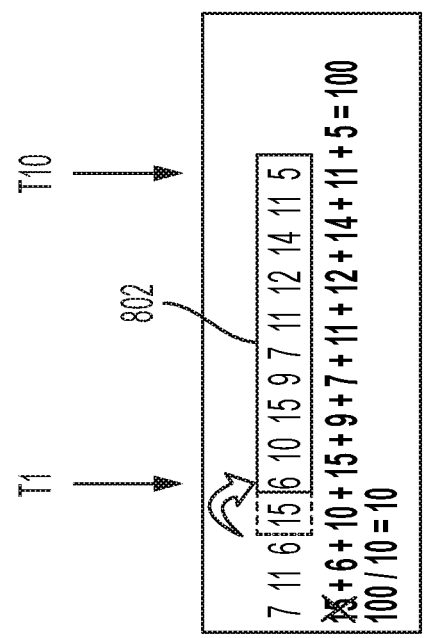
FIG. 8B is a block diagram further illustrating the moving average signal strength analysis method shown in FIG. 8A.

FIG. 7 depicts a cognitive PPG sensor activation classifier 602A, which is an example of how the PPG cognitive sensor activation module 602 (shown in FIG. 6) can be implemented. As shown in FIG. 7, the classifier 602A includes machine learning (ML) algorithms 702 and a prediction engine 704, configured and arranged as shown. In accordance with aspects of the invention, the classifier 602A and ML algorithms 702 perform an analysis that initially focuses on the signal strength of outputs from the multiple PPG devices/sensors 110. More specifically, the classifier 602A and ML algorithms 702 perform an analysis that reads all of the output signals from the multiple PPG devices 110 to compute, for each of the multiple PPG devices 110 a moving average of the strength of its output signals. Moving averages are used to gauge the direction of a current trend in a set of measurements or other data. The moving average can be calculated by averaging a number of past sampled PPG device/sensor output signal strength data points. In other words, a set of numbers representing signal strength values are samples at times (e.g., set 802 bound by sample times T1-T10 shown in FIG. 8A), added together, and then divided by the number of sampled signal strength values in the set. In the example shown in FIG. 8A, the sum of the signal strength values for the past 10 samples times T1-T10 is divided by the number of sample times (i.e., 10) to arrive at the 10-sample average signal strength of 11. As new signal strength values are sampled, the oldest data points are dropped from the set 802 and new data points come in to replace them. Thus, the data set 802 is constantly "moving" to account for new data as it becomes available. This method of calculation ensures that only the current information is being accounted for. As shown in FIG. 8B, once the new signal strength value of 5 is added to the set 802, the set 802 moves to the right and the last value of 15 is dropped from the calculation. Because the relatively small value of 5 replaces the high value of 15, the average of the data set 802 in FIG. 8B decreases from 11 to 10. Once determined, the resulting moving average signal strength values can be analyzed by the ML algorithms 702 to rank the signals from strongest to weakest. The signal strength rankings can be cut off at a level that has been determined to provide sufficient PPG signal strength to provide meaningful and reliable results from the multiple PPG devices/sensors 110. The PPG devices/sensors having output signal strength that exceeds the cut off level can be provided as one of the classification outputs 730, and more specifically as classification output 730A.

In accordance with aspects of the invention, the classifier 602A, ML algorithms 702, and the prediction engine 704 perform an additional analysis that focuses on a range of training data that will be used by the classifier 602A to create the PPG signal strength model, which will be used to generate one of the classification outputs 730, and more specifically the classification output 730B. The training data can come from a variety of sources, including, for example, the previously-described ranked signal strength of the outputs from the multiple PPG devices/sensors 110, the indoor positioning system 710, the object identification system 720, and other relevant training data (e.g., Google Maps® data, cell tower triangulation data, Wi-Fi triangulation data, etc.) provided from other training sources over the network 140. The indoor positioning system 710 includes motion sensors such as accelerometers, gyroscopes, and magnetometers that help identify whether a person wearing the band 202 (shown in FIG. 2) is seated, walking, or running. The various motion sensors also provide data that can used to help identify the orientation of the arm, wrist, or other specific part of the body where the band 202 is located. The motion sensors also help to track the travel distances and provide a more accurate position of the band 202 by increasing the resolution of the GPS with dead-reckoning algorithms.

In accordance with aspects of the invention, the classifier (or classifier algorithm) 602A is configured and arranged use the ML algorithms 702 to apply machine learning techniques to the above-described training data. In aspects of the invention, the classifier (or classifier algorithm) 602A uses the ML algorithms 702 to extract features from the training data in order to allow the prediction engine 704 to "classify" the training data and uncover (or map) relationships between and among the classified training data. The classifier 602A uses the classified training data and the uncovered/mapped relationships between and among the classified training data to create the PPG signal strength model, which is provided to the prediction engine 704 to generate a classification output 730, and more specifically, the classification output 730B. Examples of suitable implementations of the classifier 602A, the ML algorithms 702, and the prediction engine 704 include but are not limited to neural networks, support vector machines (SVMs), logistic regression, decision trees, hidden Markov Models (HMMs), etc. The learning or training performed by the classifier 602A can be supervised, unsupervised, or a hybrid that includes aspects of supervised and unsupervised learning. Supervised learning is when training data (e.g., Google Maps data) is already available and classified/labeled. Unsupervised learning is when training data is not classified/labeled so must be developed through iterations of the classifier. Unsupervised learning can utilize additional learning/training methods including, for example, clustering, anomaly detection, neural networks, deep learning, and the like. In accordance with aspects of the invention, the classification outputs 730 is feed back to the classifier 602A and used as additional training data for creating the PPG signal strength model.

In aspects of the invention, the classifier 602A can be configured to apply confidence levels (CLs) to the classification output 730B. When the classifier 602A determines that a CL in the classification output 730B is below a predetermined threshold (TH) (i.e., CL<TH), the classification output 730B can be classified as sufficiently low to justify a classification of "no confidence" or "insufficient confidence" in the classification output 730B, in which case, the computing device 130A (shown in FIG. 6) would conclude that either PPG signal strength model has misfired, or that the PPG signal strength model is not yet sufficiently trained. In either case, the classification output 730A is selected over the classification output 730B. If CL>TH, the classification output 730B can be classified as sufficiently high to justify a determination that it reliable. In this case, the classification output 730B is selected over the classification output 730A. Many different predetermined TH levels can be provided. The classification outputs 730B with CL>TH can be ranked from the highest CL>TH to the lowest CL>TH.

Figure 9:
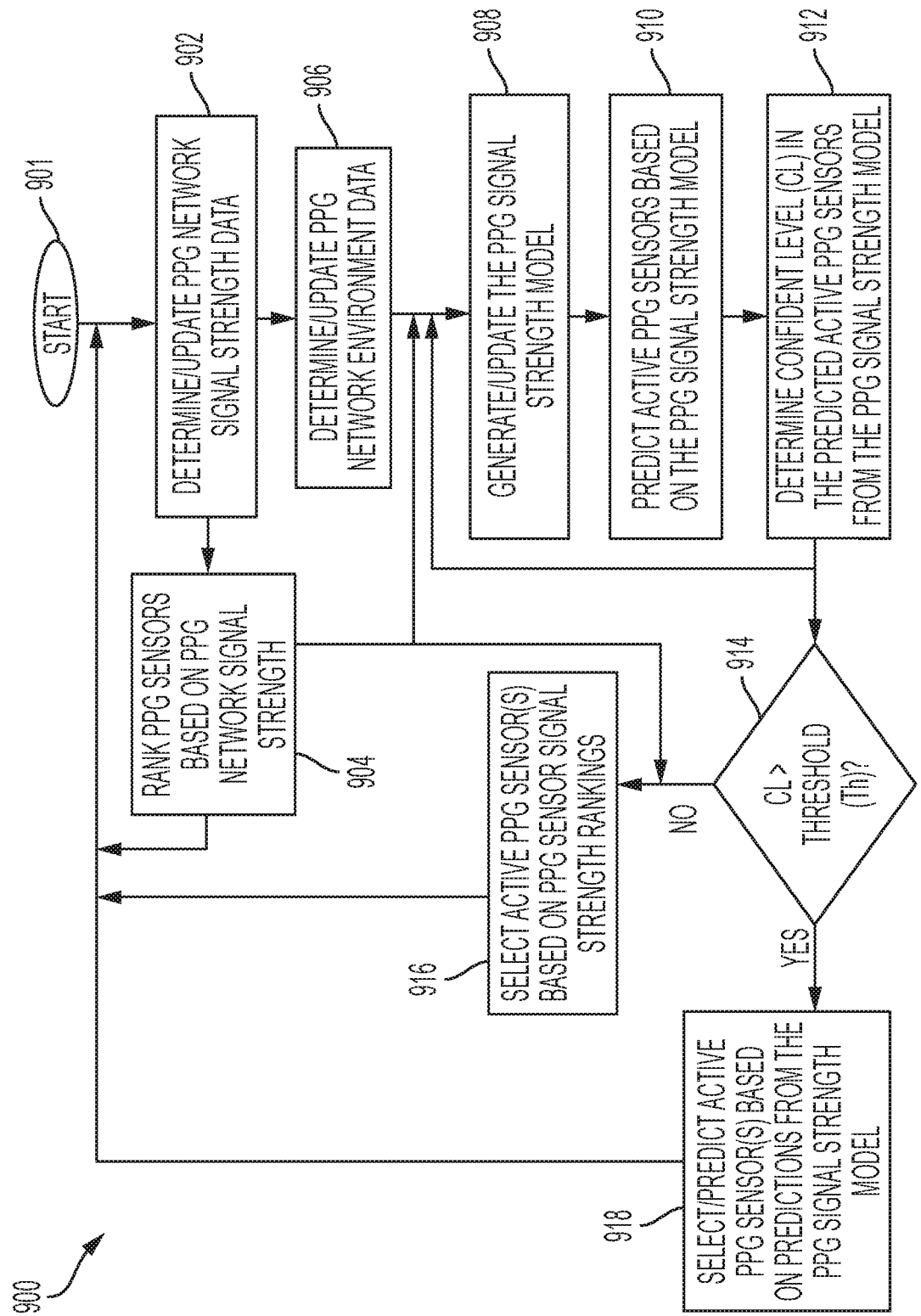
FIG. 9 is a flow diagram illustrating a methodology in accordance with embodiments of the invention.

FIG. 9 is a flow diagram illustrating a methodology 900 embodying aspects of the invention. The methodology 900 can be implemented by the computing device 130A and the cognitive PPG sensor activation module 602A shown in FIGS. 6 and 7. As shown in FIG. 9, methodology 900 starts at block 901 and moves to block 902 where the ML algorithms 702 are used to determine/update the PPG signal strength data using, for example, the moving average analysis and the reliable signal cut off analysis that are applied to the PPG device/sensor signal strength outputs. From block 902, the methodology 900 branches to block 904 where the ML algorithms 702 are used to rank the PPG signal strength data. Block 904 branches back as an input to block 902, branches as an input to block 916, and branches as an input to block 908. Block 902 also branches to block 906 where the ML algorithms 702 determine/update data that provides a variety of information about the environment in which the PPG device/sensor network 100 (shown in FIG. 1) operates. In block 908, the ML algorithm 702 and the predictive engine 704 use the data generated in blocks 906 and 904 to generate/update the PPG signal strength model. In block 910 the ML algorithms 702 and the predictive engine 704 use the PPG signal strength model to generate the classification output 730B (shown in FIG. 7). The methodology 900 moves to block 912 where a CL analysis is applied to the classification output 730B. The output from block 912 branches back as an input to block 908, and also branches as an input the decision block 914, which determines whether CL>a threshold (TH). If the answer to the inquiry at decision block 914 is no, the methodology 900 moves to block 916 where the outputs from block 904 are used to by the ML algorithms 702 and predictive engine 704 to generate the classification output 730A (shown in FIG. 7). From block 916, the methodology 900 returns to block 902. If the answer to the inquiry at the decision block 914 is yes, the methodology 900 moves to block 918 where the classification output 730B is selected over the classification output 730A. From block 918, the methodology 900 moves to block 902.

Figure 10:
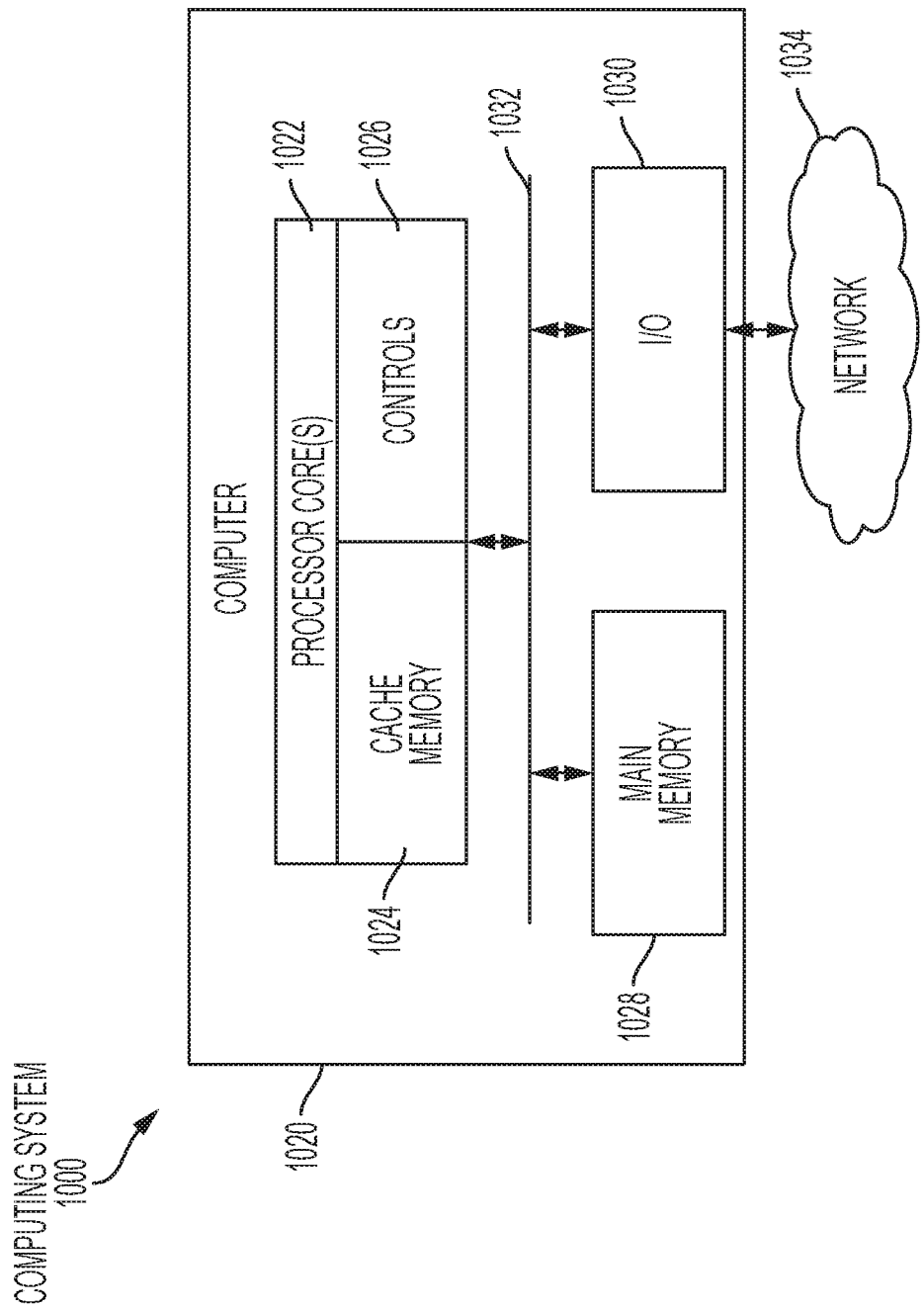
FIG. 10 is a computer system capable of implementing aspects of the invention.

FIG. 10 illustrates an example of a computer system 1000 that can be used to implement any of the computer-based components of the various embodiments of the invention described herein. The computer system 1000 includes an exemplary computing device ("computer") 1002 configured for performing various aspects of the content-based semantic monitoring operations described herein in accordance aspects of the invention. In addition to computer 1002, exemplary computer system 1000 includes network 1014, which connects computer 1002 to additional systems (not depicted) and can include one or more wide area networks (WANs) and/or local area networks (LANs) such as the Internet, intranet(s), and/or wireless communication network(s). Computer 1002 and additional system are in communication via network 1014, e.g., to communicate data between them.

Exemplary computer 1002 includes processor cores 1004, main memory ("memory") 1010, and input/output component(s) 1012, which are in communication via bus 1003. Processor cores 1004 includes cache memory ("cache") 1006 and controls 1008, which include branch prediction structures and associated search, hit, detect and update logic, which will be described in more detail below. Cache 1006 can include multiple cache levels (not depicted) that are on or off-chip from processor 1004. Memory 1010 can include various data stored therein, e.g., instructions, software, routines, etc., which, e.g., can be transferred to/from cache 1006 by controls 1008 for execution by processor 1004. Input/output component(s) 1012 can include one or more components that facilitate local and/or remote input/output operations to/from computer 1002, such as a display, keyboard, modem, network adapter, etc. (not depicted).

For the sake of brevity, conventional techniques related to semiconductor device fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices are well known and so, in the interest of brevity, many conventional steps have only be mentioned briefly herein or have been omitted entirely without providing the well-known process details.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A photoplethysmogram (PPG) structure comprising:
   a wearable component;
   a computing device physically coupled to the wearable component; and
   a network of PPG sensors physically coupled to the wearable component;
   wherein the computing device is communicatively coupled to the network of PPG sensors:
   wherein each PPG sensor of the network comprises a housing, a first light source and a light detector;
   wherein the first light source is positioned in or on the housing such that, when the housing is positioned on a surface, the housing positions an illuminating surface of the first light source at a predetermined first-light-source angle with respect to the surface;
   wherein the computing device comprises environment sensors configured to generate environment data about an environment in which the network of PPG sensors is operating;
   wherein the computing device is configured to generate signal strength data reflecting the strength of signals generated by network of PPG sensors; and
   wherein the computing device is configured to perform operations comprising:
      using a machine learning algorithm to extract features from the environmental data and the signal strength data;
      using the machine learning algorithm to generate a signal strength model representing a model of a signal strength profile of the network of PPG sensors; and
      applying signal strength readings from the network of PPG sensors to the signal strength model to classify whether or not the signal strength readings from the network of PPG sensors exceed a threshold for signal reliability.

2. The structure of claim 1, wherein the first light source and the light detectors are each in the shape of a ring.

3. The structure of claim 1, wherein:
   each PPG sensor comprises a plurality of light sources;
   the first light source is one of the plurality of light sources; and
   each of the plurality of light sources is positioned in or on the housing such that, when the housing is positioned on a surface, the housing positions an illuminating surface of each of the plurality of light sources at a predetermined light-source angle with respect to the surface;
   wherein the predetermined light-source angle tilts the illuminating surface of each of the plurality of light sources toward the light detector and the predetermined light-source angle is selected to improve a signal strength of light signals that are transmitted from the illuminating surface of each of the plurality of light sources and reach the light detector.

4. The structure of claim 1, wherein the light detector is positioned in or on the housing such that, when the housing is positioned on the surface, the housing positions a detecting surface of the light detector at a predetermined light-detector angle with respect to the surface.

5. The structure of claim 4, wherein:
   the predetermined light-detector angle tilts the detecting surface of the light detector toward the first light source and the predetermined light-detector angle is selected to improve the signal strength of light signals that are transmitted from the illuminating surface of the first light source and reach the light detector;
the predetermined first-light-source angle comprises from about 3 degrees to about 5 degrees; and
the predetermined light-detector angle comprises from about 3 degrees to about 5 degrees.

6. The structure of claim 1, wherein the wearable component comprises a band formed from material that is more flexible than the housing.

7. The structure of claim 1, wherein:
each PPG sensor of the network comprises a second light source; and
the second light source is positioned in or on the housing such that, when the housing is positioned on the surface, the housing positions an illuminating surface of the second light source at a predetermined second-light-source angle with respect to the surface;
wherein the predetermined second-light-source angle tilts the illuminating surface of the second light source toward the light detector and the predetermined second-light-source angle is selected to improve a signal strength of light signals that are transmitted from the illuminating surface of the second light source and reach the light detector.

8. The structure of claim 7, wherein:
the light detector is positioned in or on the housing such that, when the housing is positioned on the surface, the housing positions a first detecting surface of the light detector at a predetermined first-detecting-surface angle with respect to the surface; and
the light detector is positioned in or on the housing such that, when the housing is positioned on the surface, the housing positions a second detecting surface of the light detector at a predetermined second-detecting-surface angle with respect to the surface.

9. The structure of claim 8, wherein:
the predetermined first-detecting-angle tilts the first detecting surface of the light detector toward the first light source and the predetermined first-detecting-angle is selected to improve the signal strength of light signals that are transmitted from the illuminating surface of the first light source and reach the light detector;
the predetermined second-detecting-angle tilts the second detecting surface of the light detector toward the first light source and the predetermined second-detecting-angle is selected to improve the signal strength of light signals that are transmitted from the illuminating surface of the first light source and reach the light detector;
the predetermined first-light-source angle comprises from about 3 degrees to about 5 degrees;
the predetermined second-light-source angle comprises from about 3 degrees to about 5 degrees;
the predetermined first-detecting-surface angle comprises from about 3 degrees to about 5 degrees; and
the predetermined second-detecting-surface angle comprises from about 3 degrees to about 5 degrees.

10. The structure of claim 1, wherein the predetermined first-light-source angle tilts the illuminating surface of the first light source toward the light detector and the predetermined first-light-source angle is selected to improve a signal strength of light signals that are transmitted from the illuminating surface of the first light source and reach the light detector.

11. A method of forming a photoplethysmogram (PPG) structure, the method comprising:

providing a wearable component; and
providing a network of PPG sensors physically coupled to the wearable component;
wherein each PPG sensor of the network comprises a housing, a first light source and a light detector;
wherein the first light source is positioned in or on the housing such that, when the housing is positioned on a surface, the housing positions an illuminating surface of the first light source at a predetermined first-light-source angle with respect to the surface; and
providing a computing device physically coupled to the wearable component;
wherein the computing device is communicatively coupled to the network of PPG sensors;
wherein the computing device comprises environment sensors configured to generate environment data about an environment in which the network of PPG sensors is operating;
wherein the computing device is configured to generate signal strength data reflecting the strength of signals generated by network of PPG sensors; and
wherein the computing device is configured to perform operations comprising:
using a machine learning algorithm to extract features from the environmental data and the signal strength data;
using the machine learning algorithm to generate a signal strength model representing a model of a signal strength profile of the network of PPG sensors; and
applying signal strength readings from the network of PPG sensors to the signal strength model to classify whether or not the signal strength readings from the network of PPG sensors exceed a threshold for signal reliability.

12. The method of claim 11, wherein the first light source and the light detectors are each in the shape of a ring.

13. The method of claim 11, wherein:
each PPG sensor comprises a plurality of light sources;
the first light source is one of the plurality of light sources; and
each of the plurality of light sources is positioned in or on the housing such that, when the housing is positioned on a surface, the housing positions an illuminating surface of each of the plurality of light sources at a predetermined light-source angle with respect to the surface;
wherein the predetermined light-source angle tilts the illuminating surface of each of the plurality of light sources toward the light detector and the predetermined light-source angle is selected to improve a signal strength of light signals that are transmitted from the illuminating surface of each of the plurality of light sources and reach the light detector.

14. The method of claim 11, wherein the light detector is positioned in or on the housing such that, when the housing is positioned on the surface, the housing positions a detecting surface of the light detector at a predetermined light-detector angle with respect to the surface.

15. The method of claim 14, wherein:
the predetermined light-detector angle tilts the detecting surface of the light detector toward the first light source and the predetermined light-detector angle is selected to improve the signal strength of light signals that are transmitted from the illuminating surface of the first light source and reach the light detector;

the predetermined first-light-source angle comprises from about 3 degrees to about 5 degrees; and the predetermined light-detector angle comprises from about 3 degrees to about 5 degrees.

16. The method of claim 11, wherein the wearable component comprises a band formed from material that is more flexible than the housing.

17. The method of claim 11, wherein:

each PPG sensor of the network comprises a second light source; and the second light source is positioned in or on the housing such that, when the housing is positioned on the surface, the housing positions an illuminating surface of the second light source at a predetermined second-light-source angle with respect to the surface;

wherein the predetermined second-light-source angle tilts the illuminating surface of the second light source toward the light detector and the predetermined second-light-source angle is selected to improve a signal strength of light signals that are transmitted from the illuminating surface of the second light source and reach the light detector.

18. The method of claim 17, wherein:

the light detector is positioned in or on the housing such that, when the housing is positioned on the surface, the housing positions a first detecting surface of the light detector at a predetermined first-detecting-surface angle with respect to the surface; and the light detector is positioned in or on the housing such that, when the housing is positioned on the surface, the housing positions a second detecting surface of the light detector at a predetermined second-detecting-surface angle with respect to the surface.

19. The method of claim 18, wherein:

the predetermined first-detecting-angle tilts the first detecting surface of the light detector toward the first light source and the predetermined first-detecting-angle is selected to improve the signal strength of light signals that are transmitted from the illuminating surface of the first light source and reach the light detector;

the predetermined second-detecting-angle tilts the second detecting surface of the light detector toward the first light source and the predetermined second-detecting-angle is selected to improve the signal strength of light signals that are transmitted from the illuminating surface of the first light source and reach the light detector;

the predetermined first-light-source angle comprises from about 3 degrees to about 5 degrees;

the predetermined second-light-source angle comprises from about 3 degrees to about 5 degrees;

the predetermined first-detecting-surface angle comprises from about 3 degrees to about 5 degrees; and the predetermined second-detecting-surface angle comprises from about 3 degrees to about 5 degrees.

20. The method of claim 11, wherein the predetermined first-light-source angle tilts the illuminating surface of the first light source toward the light detector and the predetermined first-light-source angle is selected to improve a signal strength of light signals that are transmitted from the illuminating surface of the first light source and reach the light detector.

* * * * *